US012611182B2

(12) United States Patent
Robert et al.

(10) Patent No.: US 12,611,182 B2
(45) Date of Patent: Apr. 28, 2026

(54) COHERENTLY COMPOUNDED ULTRASOUND IMAGE GENERATION AND ASSOCIATED SYSTEMS, METHODS, AND DEVICES

(71) Applicant: KONINKLIJKE PHILIPS N.V., Eindhoven (NL)

(72) Inventors: Jean-Luc francois-marie Robert, Cambridge, MA (US); Iason Zacharias Apostolakis, Cambridge, MA (US); Oudom Somphone, Paris (FR); Fernando Quivira, Cambridge, MA (US); Jun Seob Shin, Winchester, MA (US); Faik Can Meral, Mansfield, MA (US); Francois Guy Gerard Marie Vignon, Andover, MA (US); Jason Richard Yu, Arlington, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 31 days.

(21) Appl. No.: 18/289,796

(22) PCT Filed: May 5, 2022

(86) PCT No.: PCT/EP2022/062077
§ 371 (c)(1),
(2) Date: Nov. 7, 2023

(87) PCT Pub. No.: WO2022/238218
PCT Pub. Date: Nov. 17, 2022

(65) Prior Publication Data
US 2024/0277317 A1 Aug. 22, 2024

(30) Foreign Application Priority Data
May 10, 2021 (EP) .................................... 21290027

(51) Int. Cl.
*A61B 8/00* (2006.01)
*A61B 8/14* (2006.01)
(Continued)

(52) U.S. Cl.
CPC .............. *A61B 8/5207* (2013.01); *A61B 8/14* (2013.01); *A61B 8/4488* (2013.01); *A61B 8/54* (2013.01);
(Continued)

(58) Field of Classification Search
None
See application file for complete search history.

(56) References Cited

U.S. PATENT DOCUMENTS 5,623,928 A * 4/1997 Wright ................ G01S 7/52026
73/633
5,910,115 A * 6/1999 Rigby ................. G01S 7/52046
600/443
(Continued)

OTHER PUBLICATIONS

International Search Report and Written Opinion for PCT/EP2022/062077; Mailing date: Sep. 21, 2022, 14 pages.
(Continued)

*Primary Examiner* — Nyrobi Celestine

(57) ABSTRACT
An ultrasound imaging system includes acoustic elements configured to transmit ultrasound energy and receive associated echoes. The system further includes a processor circuit in communication with the acoustic elements. The processor circuit may be configured to receive data corresponding to a set of subframes based on the echoes. The set of subframes includes a first and second subframe. The processor circuit may be configured to coherently combine data corresponding to a first portion of the first subframe and data corresponding to a first portion of the second subframe, which may both include phase information. The processor circuit may be configured to generate an image based on the
(Continued)

coherent combination of the first portion of the first subframe and the first portion of the second subframe and to output the generated image to a display in communication with the processor circuit.

13 Claims, 13 Drawing Sheets

(51) Int. Cl.
    *G01S 15/89*      (2006.01)
    *G06T 1/20*       (2006.01)

(52) U.S. Cl.
    CPC ...... *G01S 15/8927* (2013.01); *G01S 15/8995* (2013.01); *G06T 1/20* (2013.01); *G06T 2210/41* (2013.01)

(56)              References Cited

U.S. PATENT DOCUMENTS

| | | | | |
|---|---|---|---|---|
| 6,071,240 | A * | 6/2000 | Hall | G01S 7/52046 |
| | | | | 600/443 |
| 8,317,712 | B2 | 11/2012 | Burcher et al. | |
| 9,345,455 | B2 | 5/2016 | Burcher et al. | |
| 2005/0228279 | A1 * | 10/2005 | Ustuner | G01S 15/8927 |
| | | | | 600/443 |
| 2006/0173313 | A1 * | 8/2006 | Liu | G01S 15/8993 |
| | | | | 600/437 |
| 2009/0066727 | A1 * | 3/2009 | Lu | G01S 7/52085 |
| | | | | 345/643 |
| 2011/0306886 | A1 * | 12/2011 | Daft | G01S 15/8915 |
| | | | | 600/459 |
| 2012/0277589 | A1 * | 11/2012 | Katou | G01S 7/5205 |
| | | | | 600/443 |
| 2014/0058266 | A1 | 2/2014 | Call et al. | |
| 2016/0296202 | A1 * | 10/2016 | Robert | A61B 8/5207 |
| 2017/0252007 | A1 | 9/2017 | Mine et al. | |
| 2019/0072671 | A1 * | 3/2019 | Nikolov | G01S 15/8993 |
| 2019/0328368 | A1 * | 10/2019 | Pedersen | G16H 50/30 |
| 2020/0202518 | A1 * | 6/2020 | Vignon | A61B 8/4245 |
| 2020/0229797 | A1 * | 7/2020 | Yu | A61B 8/4488 |
| 2022/0155440 | A1 * | 5/2022 | Kruse | G10K 11/348 |

OTHER PUBLICATIONS

Bottenus, N. et al., "Acoustic reciprocity of spatial coherence in ultrasound imaging", IEEE Transactions on Ultrasonics, Ferroelectrics, and Frequency Control, 2015, vol. 62, No. 5, pp. 852-861.

Rau, R. et al., "Ultrasound Aberration Correction based on Local Speed-of-Sound Map Estimation", arXiv:1909.10254v1, 2019, 4 pages.

* cited by examiner

800

Control array to transmit ultrasound energy and receive echoes associated with ultrasound energy ───802

Receive data corresponding to set of subframes based on received echoes ───804

Coherently combine first portion of first subframe and first portion of second subframe ───806

Generate image based on coherent combination ───808

Output image to display ───810

COHERENTLY COMPOUNDED ULTRASOUND IMAGE GENERATION AND ASSOCIATED SYSTEMS, METHODS, AND DEVICES

CROSS-REFERENCE TO PRIOR APPLICATIONS

This application is the U.S. National Phase application under 35 U.S.C. § 371 of International Application No. PCT/EP2022/062077, filed on May 5, 2022, which claims the benefit of European Patent Application No. 21290027.8, filed on May 10, 2021. These applications are hereby incorporated by reference herein.

FIELD OF THE INVENTION

The subject matter described herein relates to a system for medical imaging. In particular, the present disclosure describes aspects related to the generation of an ultrasound image based on coherent combination of a set of subframes associated with the ultrasound image.

BACKGROUND OF THE INVENTION

An ultrasound imaging system may include a probe that houses a transducer array operable to transmit ultrasound energy and receive echoes associated with the transmitted energy. In some cases, a console device (e.g., a host system) of the ultrasound imaging system may control such ultrasound transmission and reception at the probe to generate an ultrasound image. For instance, the console device may address (e.g., control) a set of acoustic elements in the transducer array to transmit the ultrasound energy and to receive the associated echoes. In particular, the console device may interface with the probe via a set of data channels and may use the data channels to control the operation of the set of acoustic elements. In some cases, the active aperture associated with the transmission and/or reception of the ultrasound energy may be defined by the number and position of acoustic elements addressed by the console device (e.g., utilized at the transducer array) for the generation of image data. As the number of acoustic elements used to transmit ultrasound energy increases and, as a result, the size of the active aperture increases, the resolution of the resulting ultrasound image may increase. In some cases, however, the number of data channels in the ultrasound system is fixed, limiting the number of addressable acoustic elements and, therefore, the size of the active aperture. Additionally or alternatively, modifications to the ultrasound system to accommodate additional data channels may be costly in terms of time, resources, and/or the like. Accordingly, when the number of acoustic elements within a probe exceeds the number of elements addressable by a console device, a subset of the total number of acoustic elements within the probe may be used to generate an ultrasound image.

SUMMARY OF THE INVENTION

Disclosed are systems, methods, and devices for generating an ultrasound image based on the coherent combination of at least a portion of a set of subframes associated with the image. For example, an ultrasound imaging system may include a transducer array having a number of acoustic elements. The ultrasound imaging system may be configured to obtain ultrasound imaging data of an object (e.g., an anatomical object) using different subsets of the acoustic elements (e.g., sub-apertures) and/or different beam steering angles. The obtained ultrasound imaging data may correspond to a set of subframes that, when combined, produce an image of the object. In particular, the ultrasound system may be configured to address subsets of the acoustic elements and/or select the beam steering angles to then reconstruct an effective aperture exceeding the size of the sub-apertures. That is, for example, the ultrasound system may be configured to address subsets of the acoustic elements and/or select the beam steering angles such that the set of subframes may be combined to produce an image corresponding to an image that was generated (e.g., obtained) with the effective aperture. Moreover, the ultrasound imaging system may be configured to combine (e.g., sum) at least a portion of the set of subframes coherently (e.g., while the data corresponding to the set of subframes includes phase information), which may improve the resolution and/or penetration of the image in comparison with an image generated according to alternative techniques. In some cases, the ultrasound imaging system may be configured to sum the data corresponding to the set of subframes based on incoherent and coherent combination of the data. For instance, the ultrasound imaging system may weight (e.g., mask) incoherently combined subframes and coherently combined subframes to generate an ultrasound image with a blend of incoherent and coherent combination features. In particular, the incoherent combination of data corresponding to the set of subframes may reduce speckle in the ultrasound image, the coherent combination of the data corresponding to the set of subframes may improve depth and penetration of the ultrasound image, and the combination of incoherently combined data and coherently combined data may produce an ultrasound image with both reduced speckle and improved resolution and penetration.

In an exemplary aspect, an ultrasound imaging system, includes: an array of acoustic elements configured to transmit ultrasound energy and receive echoes associated with the ultrasound energy; and a processor circuit in communication with the array of acoustic elements. The processor circuit may be configured to receive data corresponding to a set of subframes based on the received echoes. The set of subframes may include a first subframe and a second subframe. The processor circuit may be configured to coherently combine data corresponding to a first portion of the first subframe and data corresponding to a first portion of the second subframe. The data corresponding to the first portion of the first subframe and the data corresponding to the first portion of the second subframe may include phase information. The processor circuit may be configured to: generate an image based on the coherent combination of the first portion of the first subframe and the first portion of the second subframe; and output the generated image to a display in communication with the processor circuit.

In some aspects, the ultrasound energy includes first ultrasound energy and second ultrasound energy, and, to transmit the ultrasound energy, the array of acoustic elements may be configured to: transmit the first ultrasound energy using a first subset of the array of acoustic elements; and transmit the second ultrasound energy using a second subset of the array of acoustic elements. In some aspects, the first subframe corresponds to the received echoes associated with the first ultrasound energy and the second subframe corresponds to the received echoes associated with the second ultrasound energy. In some aspects, to receive the echoes associated with the ultrasound energy, the array of acoustic elements may be configured to: receive echoes associated with the first ultrasound energy using the first subset of the array of acoustic elements; and receive echoes associated with the second ultrasound energy using the second subset of the array of acoustic elements.

In some aspects, the processor circuit may be configured to generate the image further based on an envelope detection of the coherent combination. In some aspects, the processor circuit may be configured to generate the image further based on a log compression of the coherent combination. In some aspects, the processor circuit may be configured to: perform a scan conversion on the data corresponding to the set of subframes. The processor circuit may be configured to coherently combine the data corresponding to the first portion of the first subframe and the data corresponding to the first portion of the second subframe further based on the scan conversion. In some aspects, the processor circuit may be configured to: incoherently combine data corresponding to a second portion of the first subframe and data corresponding to a second portion of the second subframe; and generate the image further based on the incoherent combination of the second portion of the first subframe and the second portion of the second subframe.

In some aspects, the processor circuit may be configured to generate the image further based on: generating a first image based on the coherent combination of the first portion of the first subframe and the first portion of the second subframe; generating a second image based on an incoherent combination of the first portion of the first subframe and the first portion of the second subframe; and combining the first image and the second image. In some aspects, the processor circuit may be configured to combine the first image and the second image based on a spatial frequency of the first portion of the first subframe. In some aspects, the processor circuit may be configured to combine the first image and the second image based on a location of the first portion of the first subframe within the first subframe.

In some aspects, the processor circuit may be configured to: register the first portion of the first subframe with the first portion of the second subframe. The processor circuit may be configured to coherently combine the data corresponding to the first portion of the first subframe and the data corresponding to the first portion of the second subframe further based on the registration. In some aspects, the processor circuit may be configured to register the first portion of the first subframe with the first portion of the second subframe based on: identifying a difference between the data corresponding to the first portion of the first subframe and data corresponding to a first portion of a third subframe of the set of subframes; and adjusting the data corresponding to the first portion of the first subframe based on the identified difference. In some aspects, the processor circuit includes a graphics processing unit (GPU).

In an exemplary aspect, a method includes: controlling, by a processor circuit, an array of acoustic elements in communication with the processor circuit to transmit ultrasound energy and receive echoes associated with the ultrasound energy; receiving, by the processor circuit, data corresponding to a set of subframes based on the received echoes. The set of subframes may include a first subframe and a second subframe. The method may further include coherently combining, by the processor circuit, data corresponding to a first portion of the first subframe and data corresponding to a first portion of the second subframe. The data corresponding to the first portion of the first subframe and the data corresponding to the first portion of the second subframe may include phase information. The method may further include generating, by the processor circuit, an image based on the coherent combination of the first portion of the first subframe and the first portion of the second subframe; and outputting, by the processor circuit, the generated image to a display in communication with the processor circuit. Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION OF EMBODIMENTS

Figure 1:
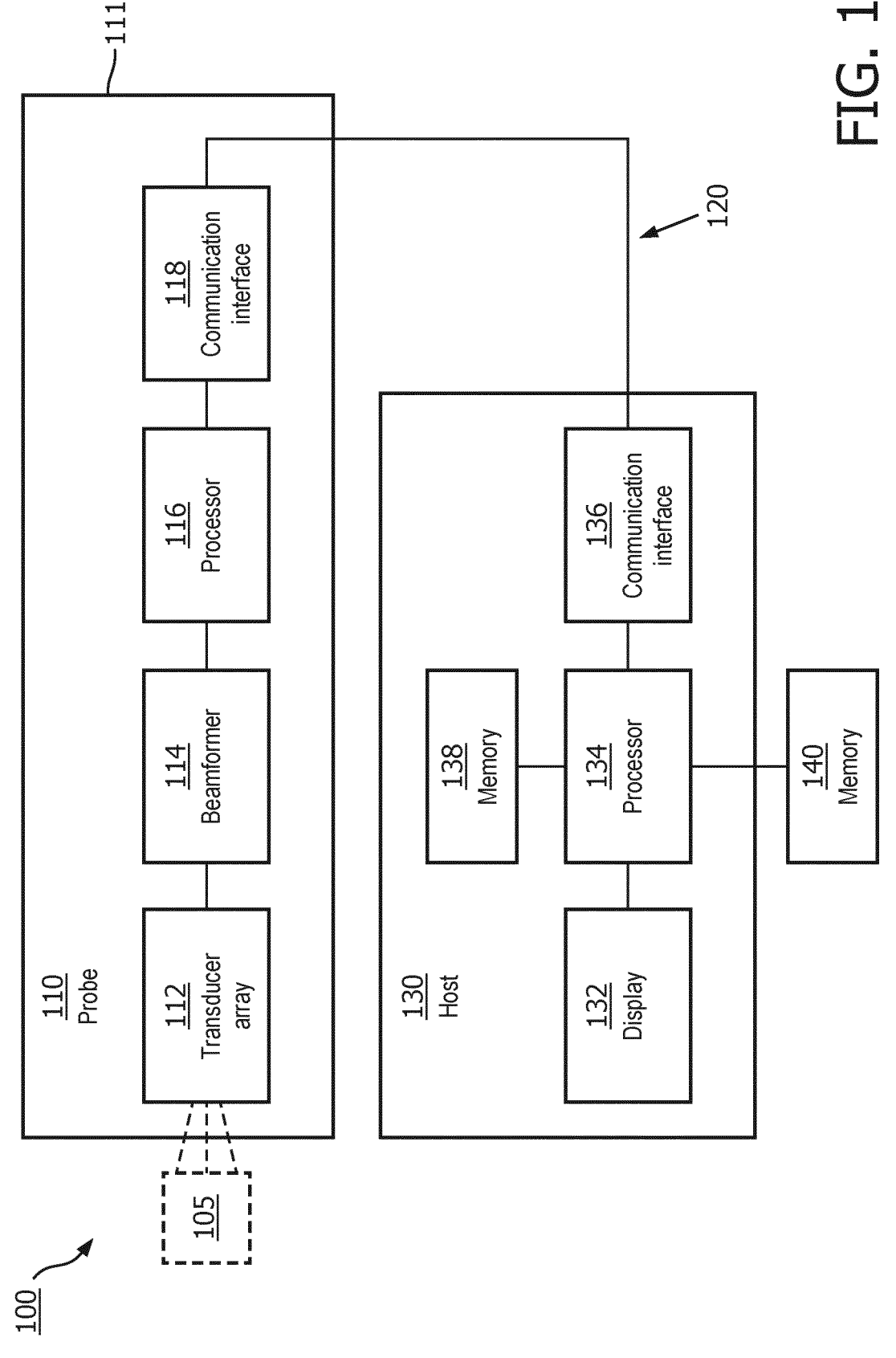
FIG. 1 is a diagrammatic schematic view of an ultrasound imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic diagram of an ultrasound imaging system 100, according to aspects of the present disclosure. The system 100 is used for scanning an area or volume of a patient's body. The system 100 includes an ultrasound imaging probe 110 in communication with a host 130 over a communication interface or link 120. The probe 110 may include a transducer array 112, a beamformer 114, a processor 116, and a communication interface 118. The host 130 may include a display 132, a processor circuit 134, a communication interface 136, and a memory 138 storing patient information. The host 130 and/or the processor 134 of the host 130 may additionally be in communication with a memory 140.

In some embodiments, the probe 110 is an external ultrasound imaging device including a housing 111 configured for handheld operation by a user. The transducer array 112 can be configured to obtain ultrasound data while the user grasps the housing 111 of the probe 110 such that the transducer array 112 is positioned adjacent to or in contact with a patient's skin. The probe 110 is configured to obtain ultrasound data of anatomy within the patient's body while the probe 110 is positioned outside of the patient's body. In some embodiments, the probe 110 can be a patch-based external ultrasound probe.

In other embodiments, the probe 110 can be an internal ultrasound imaging device and may comprise a housing 111 configured to be positioned within a lumen of a patient's body, including the patient's coronary vasculature, peripheral vasculature, esophagus, heart chamber, or other body lumen or body cavity. In some embodiments, the probe 110 may be an intravascular ultrasound (IVUS) imaging catheter or an intracardiac echocardiography (ICE) catheter. In other embodiments, probe 110 may be a transesophageal echocardiography (TEE) probe. Probe 110 may be of any suitable form for any suitable ultrasound imaging application including both external and internal ultrasound imaging.

In some embodiments, aspects of the present disclosure can be implemented with medical images of patients obtained using any suitable medical imaging device and/or modality. Examples of medical images and medical imaging devices include x-ray images (angiographic images, fluoroscopic images, images with or without contrast) obtained by an x-ray imaging device, computed tomography (CT) images obtained by a CT imaging device, positron emission tomography-computed tomography (PET-CT) images obtained by a PET-CT imaging device, magnetic resonance images (MRI) obtained by an MRI device, single-photon emission computed tomography (SPECT) images obtained by a SPECT imaging device, optical coherence tomography (OCT) images obtained by an OCT imaging device, and intravascular photoacoustic (IVPA) images obtained by an IVPA imaging device. The medical imaging device can obtain the medical images while positioned outside the patient body, spaced from the patient body, adjacent to the patient body, in contact with the patient body, and/or inside the patient body.

For an ultrasound imaging device, the transducer array 112 emits ultrasound signals towards an anatomical object 105 of a patient and receives echo signals reflected from the object 105 back to the transducer array 112. The transducer array 112 can include any suitable number of acoustic elements, including one or more acoustic elements and/or a plurality of acoustic elements. In some instances, the transducer array 112 includes a single acoustic element. In some instances, the transducer array 112 may include an array of acoustic elements with any number of acoustic elements in any suitable configuration. For example, the transducer array 112 can include between 1 acoustic element and 10000 acoustic elements, including values such as 2 acoustic elements, 4 acoustic elements, 36 acoustic elements, 64 acoustic elements, 128 acoustic elements, 500 acoustic elements, 812 acoustic elements, 1000 acoustic elements, 1920 acoustic elements, 3000 acoustic elements, 8000 acoustic elements, and/or other values both larger and smaller. In some instances, the transducer array 112 may include an array of acoustic elements with any number of acoustic elements in any suitable configuration, such as a linear array, a planar array, a curved array, a curvilinear array, a circumferential array, an annular array, a phased array, a matrix array, a one-dimensional (1D) array, a 1.x dimensional array (e.g., a 1.5D array), or a two-dimensional (2D) array. The array of acoustic elements (e.g., one or more rows, one or more columns, and/or one or more orientations) can be uniformly or independently controlled and activated. The transducer array 112 can be configured to obtain one-dimensional, two-dimensional, and/or three-dimensional images of a patient's anatomy. In some embodiments, the transducer array 112 may include a piezoelectric micromachined ultrasound transducer (PMUT), capacitive micromachined ultrasonic transducer (CMUT), single crystal, lead zirconate titanate (PZT), PZT composite, other suitable transducer types, and/or combinations thereof.

The object 105 may include any anatomy or anatomical feature, such as a diaphragm, blood vessels, nerve fibers, airways, mitral leaflets, cardiac structure, abdominal tissue structure, appendix, large intestine (or colon), small intestine, kidney, liver, and/or any other anatomy of a patient. In some aspects, the object 105 may include at least a portion of a patient's large intestine, small intestine, cecum pouch, appendix, terminal ileum, liver, epigastrium, and/or psoas muscle. The present disclosure can be implemented in the context of any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood vessels, blood, chambers or other parts of the heart, abdominal organs, and/or other systems of the body. In some embodiments, the object 105 may include malignancies such as tumors, cysts, lesions, hemorrhages, or blood pools within any part of human anatomy. The anatomy may be a blood vessel, as an artery or a vein of a patient's vascular system, including cardiac vasculature, peripheral vasculature, neural vasculature, renal vasculature, and/or any other suitable lumen inside the body. In addition to natural structures, the present disclosure can be implemented in the context of man-made structures such as, but without limitation, heart valves, stents, shunts, filters, implants and other devices.

The beamformer 114 is coupled to the transducer array 112. The beamformer 114 controls the transducer array 112, for example, for transmission of the ultrasound signals and reception of the ultrasound echo signals. In some embodiments, the beamformer 114 may apply a time-delay to signals sent to individual acoustic transducers within an array in the transducer array 112 such that an acoustic signal is steered in any suitable direction propagating away from the probe 110. The beamformer 114 may further provide image signals to the processor 116 based on the response of the received ultrasound echo signals. The beamformer 114 may include multiple stages of beamforming. The beamforming can reduce the number of signal lines for coupling to the processor 116. In some embodiments, the transducer array 112 in combination with the beamformer 114 may be referred to as an ultrasound imaging component.

The processor 116 is coupled to the beamformer 114. The processor 116 may also be described as a processor circuit, which can include other components in communication with the processor 116, such as a memory, beamformer 114, communication interface 118, and/or other suitable components. The processor 116 may include a central processing unit (CPU), a graphical processing unit (GPU), a digital signal processor (DSP), an application specific integrated circuit (ASIC), a controller, a field programmable gate array (FPGA) device, another hardware device, a firmware device, or any combination thereof configured to perform the operations described herein. The processor 116 may also be implemented as a combination of computing devices, e.g., a combination of a DSP and a microprocessor, a plurality of microprocessors, one or more microprocessors in conjunction with a DSP core, or any other such configuration. The processor 116 is configured to process the beamformed image signals. For example, the processor 116 may perform filtering and/or quadrature demodulation to condition the image signals. The processor 116 and/or 134 can be configured to control the array 112 to obtain ultrasound data associated with the object 105.

The communication interface 118 is coupled to the processor 116. The communication interface 118 may include one or more transmitters, one or more receivers, one or more transceivers, and/or circuitry for transmitting and/or receiving communication signals. The communication interface 118 can include hardware components and/or software components implementing a particular communication protocol suitable for transporting signals over the communication link 120 to the host 130. The communication interface 118 can be referred to as a communication device or a communication interface module.

The communication link 120 may be any suitable communication link. For example, the communication link 120 may be a wired link, such as a universal serial bus (USB) link or an Ethernet link. Alternatively, the communication link 120 may be a wireless link, such as an ultra-wideband (UWB) link, an Institute of Electrical and Electronics Engineers (IEEE) 802.11 WiFi link, or a Bluetooth link.

At the host 130, the communication interface 136 may receive the image signals. The communication interface 136 may be substantially similar to the communication interface 118. The host 130 may be any suitable computing and display device, such as a workstation, a personal computer (PC), a laptop, a tablet, or a mobile phone.

The processor 134 is coupled to the communication interface 136. The processor 134 may also be described as a processor circuit, which can include other components in communication with the processor 134, such as the memory 138, the communication interface 136, and/or other suitable components. The processor 134 may be implemented as a combination of software components and hardware components. The processor 134 may include a central processing unit (CPU), a graphics processing unit (GPU), a digital signal processor (DSP), an application-specific integrated circuit (ASIC), a controller, an FPGA device, another hardware device, a firmware device, or any combination thereof configured to perform the operations described herein. The processor 134 may also be implemented as a combination of computing devices, e.g., a combination of a DSP and a microprocessor, a plurality of microprocessors, one or more microprocessors in conjunction with a DSP core, or any other such configuration. The processor 134 can be configured to generate image data from the image signals received from the probe 110. The processor 134 can apply advanced signal processing and/or image processing techniques to the image signals. An example of image processing includes conducting a pixel level analysis to evaluate whether there is a change in the color of a pixel, which may correspond to an edge of an object (e.g., the edge of an anatomical feature). In some embodiments, the processor 134 can form a three-dimensional (3D) volume image from the image data. In some embodiments, the processor 134 can perform real-time processing on the image data to provide a streaming video of ultrasound images of the object 105.

The memory 138 is coupled to the processor 134. The memory 138 may be any suitable storage device, such as a cache memory (e.g., a cache memory of the processor 134), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, solid state drives, other forms of volatile and non-volatile memory, or a combination of different types of memory.

The memory 138 can be configured to store patient information, measurements, data, or files relating to a patient's medical history, history of procedures performed, anatomical or biological features, characteristics, or medical conditions associated with a patient, computer readable instructions, such as code, software, or other application, as well as any other suitable information or data. The memory 138 may be located within the host 130. Patient information may include measurements, data, files, other forms of medical history, such as but not limited to ultrasound images, ultrasound videos, and/or any imaging information relating to the patient's anatomy.

Any or all of the previously mentioned computer readable media, such as patient information, code, software, or other applications, or any other suitable information or data may also be stored the memory 140. The memory 140 may serve a substantially similar purpose to the memory 138 but may not be located within the host 130. For example, in some embodiments, the memory may be a cloud-based server, an external storage device, or any other device for memory storage. The host 130 may be in communication with the memory 140 by any suitable means as described. The host 130 may be in communication with the memory 140 continuously or they may be in communication intermittently upon the request of the host 130 or a user of the ultrasound system 100.

The host 130 may be in communication with the memory 140 via any suitable communication method. For example, the host 130 may be in communication with the memory 140 via a wired link, such as a USB link or an Ethernet link. Alternatively, the host 130 may be in communication with the memory 140 via a wireless link, such as an UWB link, an IEEE 802.11 WiFi link, or a Bluetooth link.

The display 132 is coupled to the processor circuit 134. The display 132 may be a monitor or any suitable display.

The display 132 is configured to display the ultrasound images, image videos, and/or any imaging information of the object 105.

The system 100 may be used to assist a sonographer in performing an ultrasound scan. The scan may be performed in a, or at a, point-of-care setting. In some instances, the host 130 is a console or movable cart. In some instances, the host 130 may be a mobile device, such as a tablet, a mobile phone, or portable computer.

Figure 2:
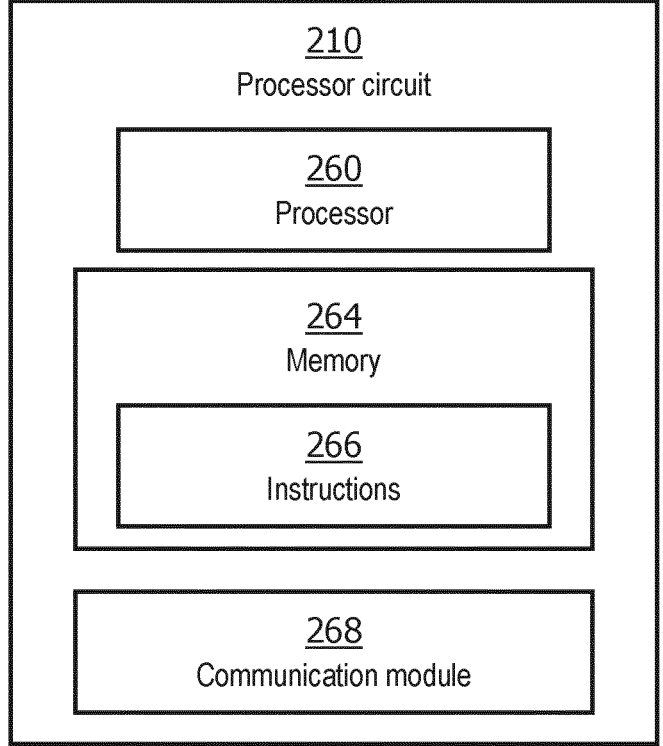
FIG. 2 is a schematic diagram of a processor circuit, according to aspects of the present disclosure.

FIG. 2 is a schematic diagram of a processor circuit 210, according to aspects of the present disclosure. The processor circuit 210 may be implemented in the probe 110, the host system 130 of FIG. 1, or any other suitable location. One or more processor circuits can be configured to carry out the operations described herein. The processor circuit 210 can be part of the circuitry 116 and/or circuitry 134 or may be separate circuitry. In an example, the processor circuit 210 may be in communication with the transducer array 112, beamformer 114, communication interface 118, communication interface 136, memory 138, memory 140, and/or the display 132, as well as any other suitable component or circuit within ultrasound system 100. As shown, the processor circuit 210 may include a processor 260, a memory 264, and a communication module 268. These elements may be in direct or indirect communication with each other, for example via one or more buses.

The processor 260 may include a CPU, a GPU, a DSP, an application-specific integrated circuit (ASIC), a controller, an FPGA, another hardware device, a firmware device, or any combination thereof configured to perform the operations described herein. The processor 260 may also be implemented as a combination of computing devices, e.g., a combination of a DSP and a microprocessor, a plurality of microprocessors, one or more microprocessors in conjunction with a DSP core, or any other such configuration. The processor 260 may also implement various deep learning networks, which may include a hardware or a software implementation.

The memory 264 may include a cache memory (e.g., a cache memory of the processor 260), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 264 includes a non-transitory computer-readable medium. The memory 264 may store instructions 266. The instructions 266 may include instructions that, when executed by the processor 260, cause the processor 260 to perform the operations described herein with reference to the probe 110 and/or the host 130 (FIG. 1). Instructions 266 may also be referred to as code. The terms "instructions" and "code" should be interpreted broadly to include any type of computer-readable statement(s). For example, the terms "instructions" and "code" may refer to one or more programs, routines, sub-routines, functions, procedures, etc. "Instructions" and "code" may include a single computer-readable statement or many computer-readable statements. Instructions 266 may include various aspects of image generation, such as coherent combination of multiple subframes of an image, or various other instructions or code.

The communication module 268 can include any electronic circuitry and/or logic circuitry to facilitate direct or indirect communication of data between the processor circuit 210, the probe 110, and/or the display 132. In that regard, the communication module 268 can be an input/output (I/O) device. In some instances, the communication module 268 facilitates direct or indirect communication between various elements of the processor circuit 210 and/or the probe 110 (FIG. 1) and/or the host 130 (FIG. 1).

Figure 3:
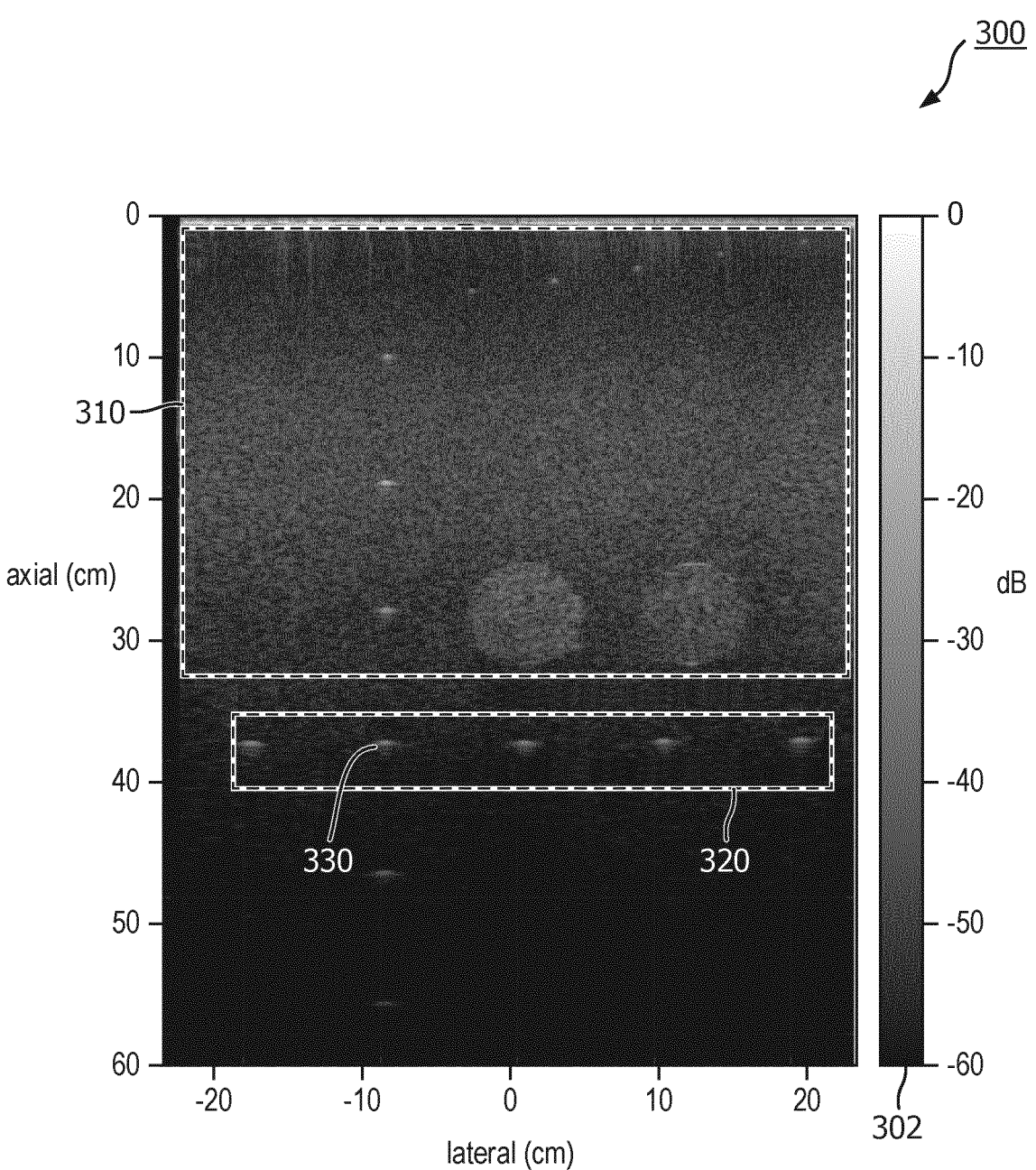
FIG. 3 is an ultrasound image, according to aspects of the present disclosure.

FIG. 3 illustrates an exemplary ultrasound image 300 (e.g., a B-mode ultrasound image) obtained without transmit beam steering (e.g., with a beam steering angle of 0°). In particular, FIG. 3 shows an ultrasound image that may be obtained by transmitting ultrasound energy along a straight path (e.g., perpendicularly) from a transducer array, such as transducer array 112 (FIG. 1). To that end, the ultrasound image 300 may be produced based on echoes associated with the ultrasound energy that are reflected by an imaged object. As further shown, the ultrasound image 300 is shown with respect to an axial distance in centimeters (cm), which may represent a distance (e.g., a depth) from the transducer array, and a lateral distance, which may correspond to a position along the transducer array (e.g., a position of an acoustic element of the transducer array). The intensity of the ultrasound imaging data (e.g., the received echoes) is also shown in decibels (dB) according to the color-coded scale 302.

In some cases, ultrasound images may include distortions, such as noise, a lack of resolution, and/or the like, that may limit the accuracy, reliability, and/or usefulness of ultrasound imaging for clinical practices. For instance, an ultrasound image may include speckle appearing as noise and/or distortion and resulting from random scattering of ultrasound energy and/or echoes. As an illustrative example, in the region 310 (e.g., a near-field region) of the ultrasound image 300, speckle is visible as the textured or noisy appearance. To that end, in the region 310, the ultrasound image 300 includes a non-uniform background resulting from speckle. Further, resolution of an ultrasound image may vary over the depth of the image (e.g., with respect to the axial distance imaged). For instance, in comparison with points within the region 310, which encompasses a relatively shallower depth, points within the region 320 (e.g., a far-field region), which encompasses a relatively greater depth, appear less resolved. In particular, instead of appearing as a relatively resolved (e.g., sharp) circle, the outline of the object 330 is spread and indistinct. Thus, as illustrated by each of the speckle and lack of resolution in the ultrasound image 300 (e.g., with respect to region 310 and 320, respectively), distortion in an ultrasound image may obscure features of the imaged object, which may impact a clinician's ability to interpret the image and/or to make an accurate diagnosis.

Figure 4:
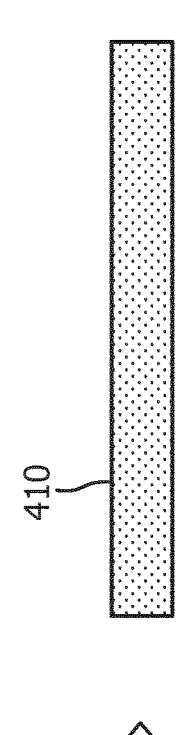
FIG. 4 is a diagrammatic view of the combination of a set of sub-apertures to form an effective aperture, according to aspects of the present disclosure.
Figure 4:
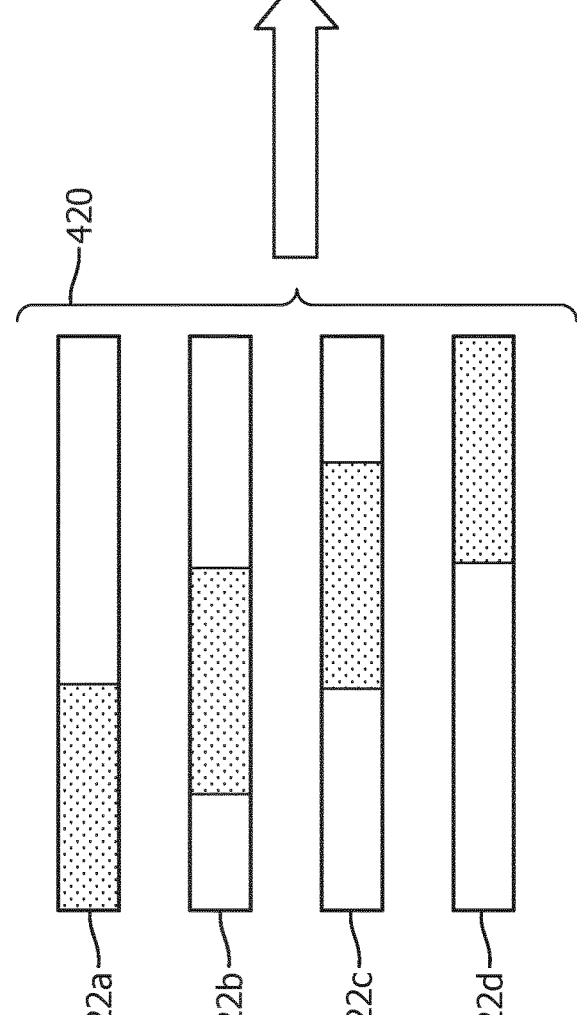

FIG. 4 diagrammatically illustrates the generation of an effective aperture 410 from a set of sub-apertures 420. In particular, FIG. 4 illustrates the use of different subsets of acoustic elements of a transducer array (e.g., transducer array 112) that may be used to reconstruct (e.g., produce) an effective aperture 410 spanning the full aperture of the transducer array (e.g., an aperture using each of the acoustic elements of the transducer array). For instance, each of the sub-apertures 422a-d may be produced by activating a subset of the acoustic elements of a transducer array. More specifically, the shaded portion of each of the sub-apertures 422a-d may represent the acoustic elements of the transducer array that are used to transmit ultrasound energy and receive echoes associated with the transmitted ultrasound energy, while the unshaded portion of each of the sub-apertures 422a-d may represent the remaining acoustic elements within the transducer array. In some embodiments, the first sub-aperture 422*a* of the transducer array may be used at a first time to obtain first ultrasound data, the second sub-aperture 422*b* of the transducer array may be used at a second time to obtain second ultrasound data, the third sub-aperture 422*c* of the transducer array may be used at a third time to obtain third ultrasound data, and the fourth sub-aperture 422*d* of the transducer array may be used at a fourth time to obtain fourth ultrasound data. For instance, the acoustic elements of corresponding to the set of sub-apertures may be fired (e.g., used to transmit ultrasound energy) consecutively. Further, the first, second, third, and fourth ultrasound data may correspond to a subframe of an ultrasound image. That is, for example, an image (e.g., an image frame) may be generated based on the combination of the subframes corresponding to each of the set of sub-apertures 420. Moreover, the generated image may correspond to an image that was generated with the effective aperture 410. For instance, the width of the generated image may correspond to the width of an image generated with a full aperture of the transducer array.

Figure 5A:
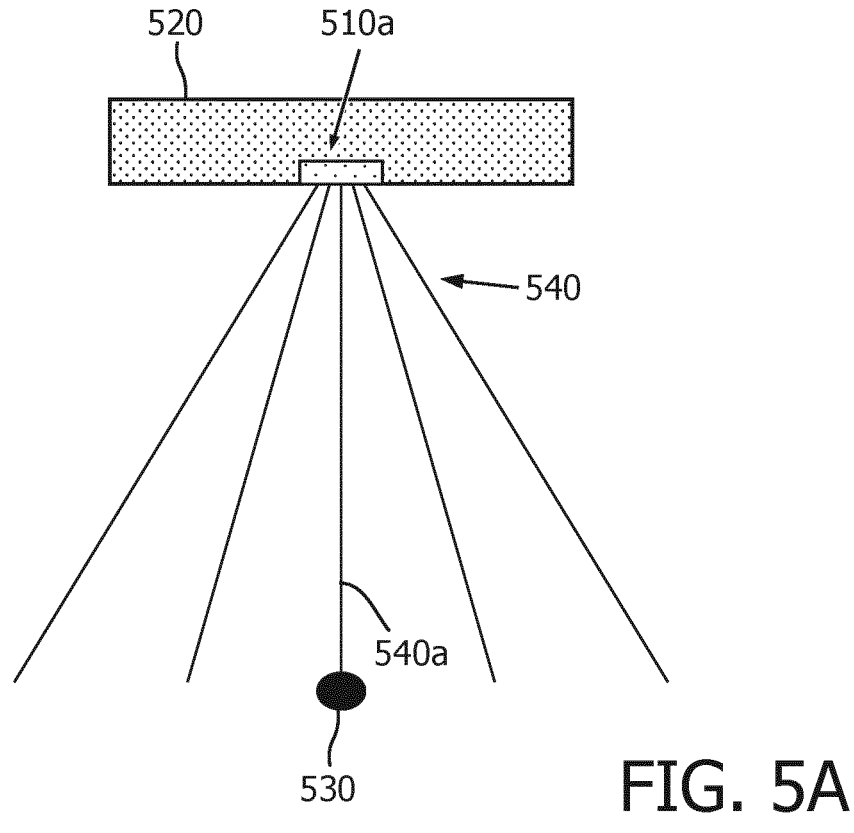
FIG. 5a is a diagrammatic view of ultrasound imaging using a sub-aperture, according to aspects of the present disclosure.
Figure 5B:
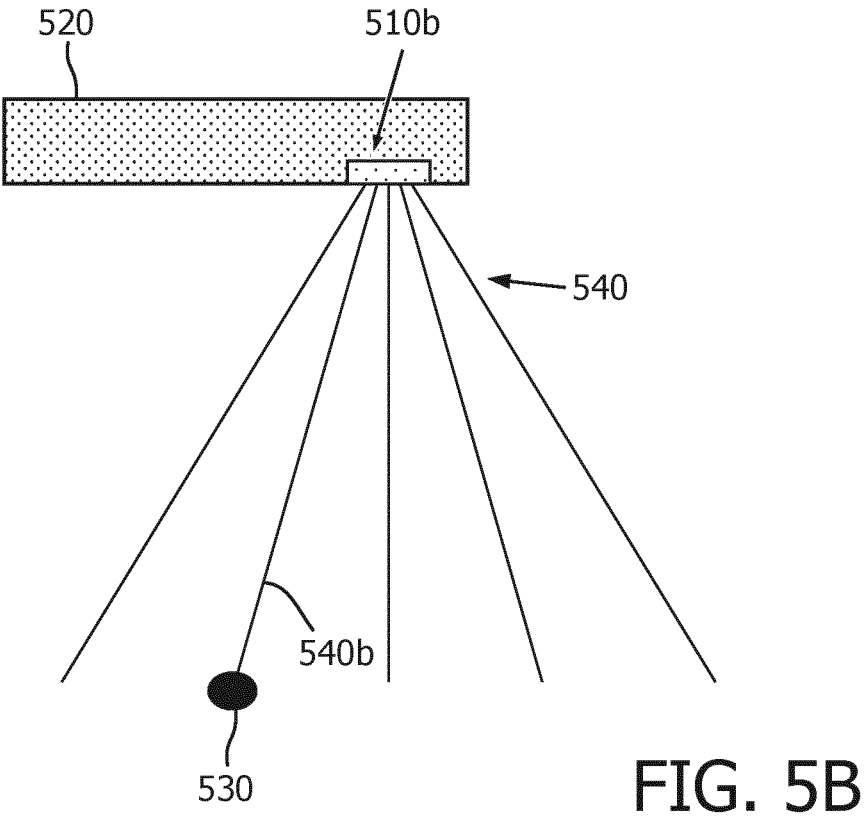
FIG. 5b is a diagrammatic view of ultrasound imaging using a sub-aperture, according to aspects of the present disclosure

FIGS. 5A-5B further illustrate the use of sub-apertures to generate an image. In particular, FIG. 5A illustrates the use of a first sub-aperture 510*a*, which may be substantially similar to a sub-aperture 422*a-d*, of a transducer array 520, which may be substantially similar to transducer array 112, to image an object 530. FIG. 5B illustrates the use of a second sub-aperture 510*b* of the transducer array 520 to image the object 530. As further illustrated, each of the sub-apertures 510*a-b* may be used to transmit ultrasound energy using a plurality of angles 540 (e.g., a plurality of beam steering angles). That is, for example, transmit beam steering may be used for the transmission of ultrasound energy from the sub-apertures 510*a-d*. In some embodiments, for example, a beam steering angle of 0°, 5°, −5°, 10°, −10°, or any other suitable angle may be used to transmit ultrasound energy.

In some embodiments, the ultrasound image data resulting from the transmission of ultrasound energy at different combinations of sub-aperture (510*a-b*) and angle of the plurality of angles 540 may correspond to a respective subframe of a set of subframes that may be combined (e.g., compounded) to generate an image of the object 530. As an illustrative example, ultrasound image data obtained via the first sub-aperture 510*a* using a first angle 540*a* may correspond to a first subframe of an image of the object 530, and ultrasound image data obtained via the second sub-aperture 510*b* using a second angle 540*b* may correspond to a second subframe of an image of the object 530. To that end, both the first subframe and the second subframe may capture features of the same object (e.g., object 530) from respective sub-apertures and angles. Moreover, the combination of the first and second subframe may reduce distortion in the resulting image in comparison with an image generated using a single aperture and/or a single angle to transmit ultrasound energy. An example of image data combination is described in U.S. Pat. No. 8,317,712, filed Apr. 17, 2017, titled "Retrospective Dynamic Transmit Focusing for Spatial Compounding," the entirety of which is hereby incorporated by reference. Mechanisms of combining (e.g., compounding) subframes of an image are described in greater detail herein.

Figure 6:
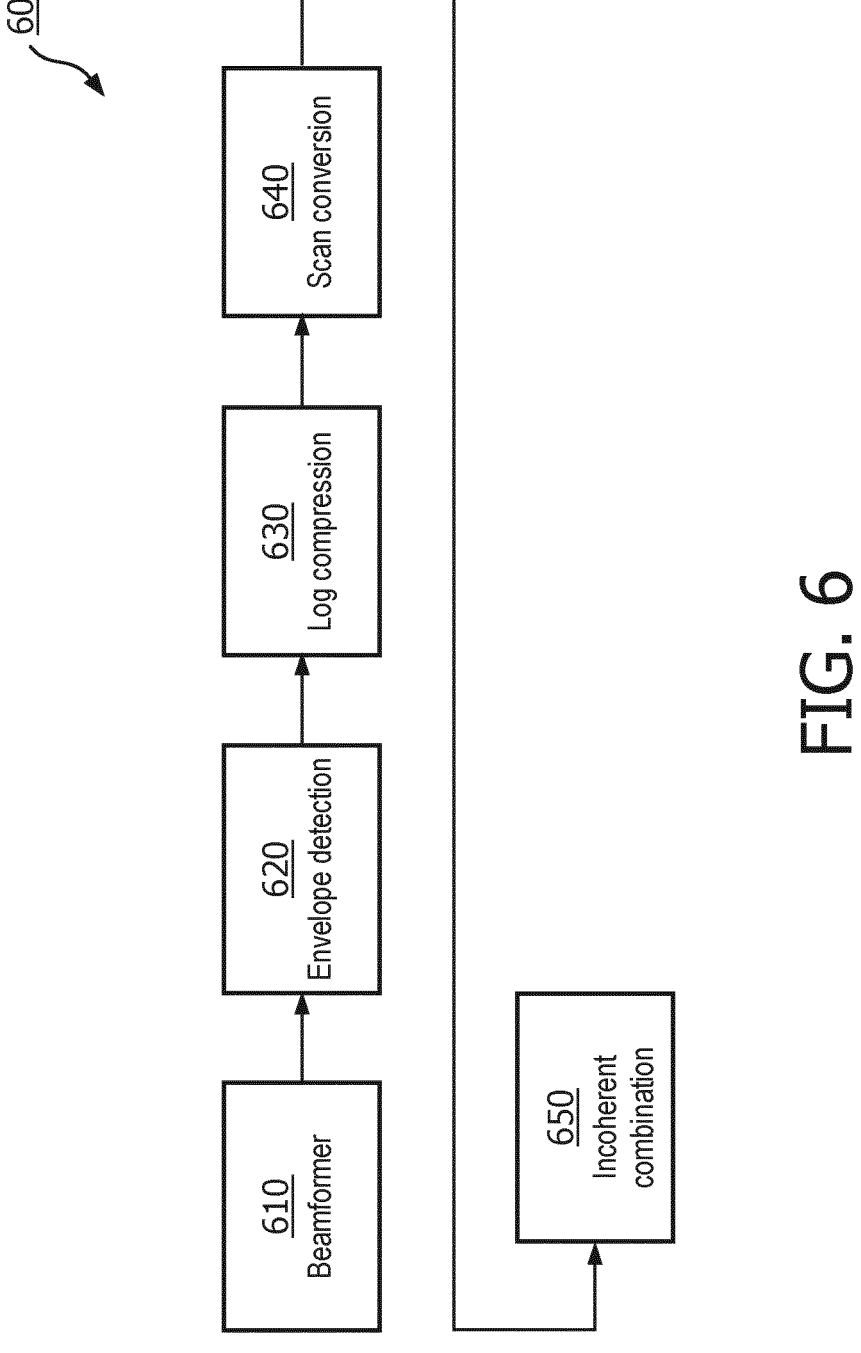
FIG. 6 is a block diagram of a signal pathway for generating an ultrasound image using incoherent combination of a set of subframes, according to aspects of the present disclosure.

FIG. 6 is a block diagram of a signal pathway 600 for generating an ultrasound image using incoherent combination of a set of subframes, according to embodiments of the present disclosure. The signal pathway 600 may be associated with a method, or process, for image generation. It will be understood that the elements of the signal pathway 600 may comprise computer program code or instructions executable by a processor circuit, such as the processor circuit 210 shown in FIG. 2. For example, in some embodiments, the elements of the signal pathway 600 comprise different processing (e.g., software) modules. In some embodiments, the elements of the signal pathway 600 comprise different hardware components.

In some embodiments, the components and/or operations of the signal pathway 600 are implemented by the probe 110 and/or the host 130 shown in FIG. 1. In particular, components of the signal pathway 600 may be implemented by the beamformer 114, the processor 116, the communication interface 118, the communication interface 136, and/or the processor 134. In some embodiments, for example, the components of the signal pathway 600 are distributed between the probe 110, and the host 130. Moreover, the components of the signal pathway 600 can be implemented via a combination of hardware and software components, and may be executed by the processor circuit 210 described above with respect to FIG. 2. For instance, in some embodiments, one or more components and/or operations of the signal pathway 600 can be executed by a GPU.

In some embodiments, ultrasound data may be received (e.g., input to) the signal pathway 600. For instance, the signal pathway 600 may receive data corresponding to a set of subframes based on received echoes associated with ultrasound energy transmitted by an array of acoustic elements (e.g., transducer array 112). In particular, the data corresponding to the set of subframes may be associated with echoes associated with ultrasound energy transmitted by a set of sub-apertures and/or at a set of different angles, as described herein. The data corresponding to the set of subframes may include analog or digital data. For instance, in some cases, the signal pathway 600 may receive raw analog electrical signals from the array of acoustic elements. In such cases, one or more of the operations of the signal pathway 600 may be performed on the analog signals. Additionally or alternatively, the signal pathway 600 may include or be in communication with an analog-to-digital converter (ADC), which may sample the analog signals to provide digital subframe data.

As illustrated, the signal pathway 600 may include a beamformer 610. The beamformer 610 may be substantially similar to the beamformer 114 of FIG. 1. To that end, in some embodiments, the beamformer 610 may be included in an ultrasound probe (e.g., probe 110). In any case, the data corresponding to the set of subframes may be beamformed at the beamformer 610. For instance, the beamformer 610 may perform a coherent delay-and-sum operation on the data to provide beamformed signals. In some embodiments, the beamformer 610 may include multiple stages of beamforming. Further, in some embodiments, the beamforming can reduce the number of signal lines associated with the data corresponding to the set of subframes for coupling to a host (e.g., host 130). Moreover, as described above, the data corresponding to the set of subframes may include analog or digital signals. Thus, the beamformer 610 may perform beamforming on the data in one or both of the analog or digital domain.

After the data corresponding to the set of subframes is beamformed, the data corresponding to the set of subframes may be output to an envelope detection module 620. The envelope detection module 620 may be implemented as an envelope detector (e.g., a rectifier, a filter, and/or the like) that may output the envelope of the data corresponding to the set of subframes. As the envelope of the data corresponding to the set of subframes corresponds to amplitude, and not phase information associated with the data, the envelope detection module 620 may suppress or remove the phase information associated with the data corresponding to the set of subframes.

In addition to or in the alternative of the ultrasound imaging system 100 including an envelope detector for the envelope detection module 620, the beamformer 114 may perform a baseband conversion and/or demodulation on the data corresponding to the set of subframes. In some embodiments, the beamformer 114 may include a rectifier configured to convert the real-valued RF samples in the image signals to baseband (BB) signal signals or data including complex in-phase, quadrature-phase (IQ) pairs. The rectifier may perform down-conversion, low-pass filtering, and/or decimation. The down-conversion converts the RF output signal data from the RF to BB, for example, by down-mixing the RF signals with two sinusoidal signals with a 90 degrees phase difference. To that end, the envelope detection may be performed at the beamformer 114. Additionally or alternatively, a GPU (e.g., a processor circuit 210) may be implemented to perform envelope detection or a portion thereof on the data corresponding to the set of subframes.

The signal pathway 600 may further include a log compression module 630 configured to perform log compression on the data corresponding to the set of subframes. More specifically, the log compression module 630 may perform log compression on the data corresponding to the set of subframes after the envelope detection is performed (e.g., via the envelope detection module 620). To that end, the log compression may be applied to the envelope of the data corresponding to the set of subframes, which may capture amplitude, but not phase information associated with the data corresponding to the set of subframes. In some embodiments, a processor circuit, such as processor circuit 210 of FIG. 2, may implement the log compression module 630. In some embodiments, for example, a GPU may perform log compression on the data corresponding to a set of subframes.

A scan conversion module 640 may be coupled to the log compression module 630 and may perform scan conversion on the image data (e.g., the data corresponding to the set of subframes) output by the log compression module 630 to a suitable display format. In an example, the image data may be in a polar coordinate and the scan conversion module 640 may convert the image data into Cartesian coordinates for display. In some embodiments, a processor circuit, such as processor circuit 210 of FIG. 2, may implement the scan conversion module 640. In some embodiments, for example, a GPU may perform scan conversion on the data corresponding to a set of subframes.

The signal pathway 600 further includes an incoherent combination module 650. The incoherent combination module 650 may be configured to incoherently combine (e.g., compound) the data corresponding to the set of subframes. For instance, the incoherent combination module 650 may sum (e.g., average) data corresponding to a first subframe of the set of subframes and data corresponding to a second subframe of the set of subframes to incoherently combine the data corresponding to the set of subframes. Moreover, incoherent combination of image data may correspond to the summing (e.g., averaging) of data corresponding to the set of subframes that lacks phase information. To that end, while the illustrated incoherent combination module is positioned at the end of the signal pathway, the incoherent combination module may additionally or alternatively be positioned in any portion of the signal pathway 600 where the data corresponding to the set of subframes lacks phase information, such as any portion of the signal pathway 600 following envelope detection (e.g., at the envelope detection module 620).

In some embodiments, the incoherent combination module 650 may be implemented as a summer, such as a digital or analog summer. Additionally or alternatively, a processor circuit, such as processor circuit 210 of FIG. 2, may implement the incoherent combination module 650. In some embodiments, for example, a GPU may incoherently combine data corresponding to a set of subframes.

While the signal pathway 600 is illustrated and described herein as including a certain set of components and/or involving certain operations, embodiments are not limited thereto. To that end, additional components and/or operations may be included and/or components and/or operations may be omitted. For instance, the signal pathway 600 may additionally or alternatively include an ADC (e.g., involve analog-to-digital conversion), any suitable filter (e.g., a low pass filter, a high pass filter, a band pass filter, and/or the like), a buffer and/or memory device, which may temporarily store and/or duplicate data, and/or the like. In some embodiments, for example, image data may be buffered at a buffer until data corresponding to each of the set of subframes is received at the signal pathway 600 and/or received at a particular portion of the signal pathway 600. Moreover, while the signal pathway 600 is illustrated in a particular order, one or more of the components and/or operations may be performed in a different order or may be performed in parallel.

Figure 7:
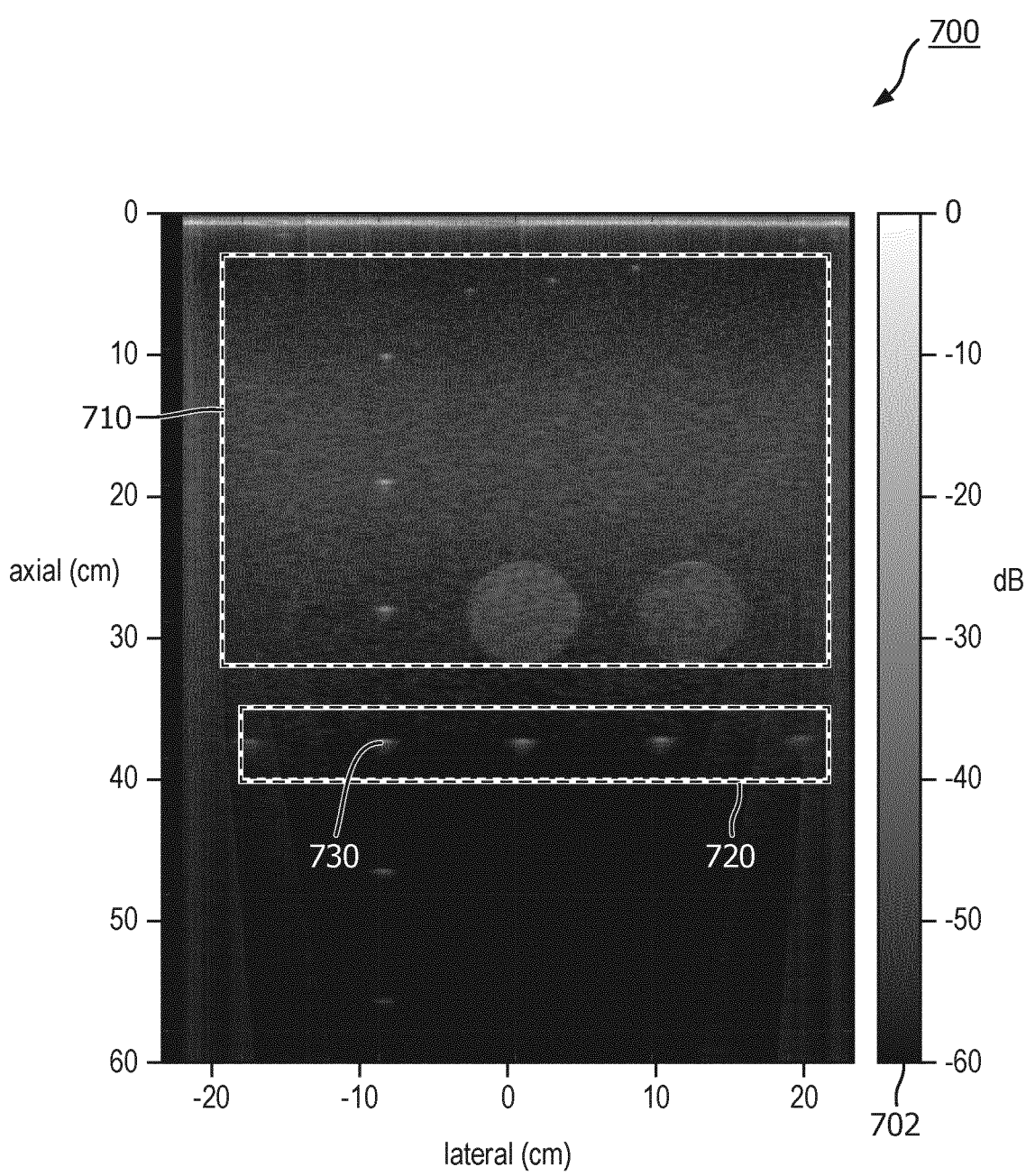
FIG. 7 is an ultrasound image, according to aspects of the present disclosure, according to aspects of the present disclosure.

FIG. 7 illustrates an exemplary ultrasound image 700 (e.g., a B-mode ultrasound image) generated based on incoherent combination of data corresponding to a set of subframes, in accordance with the techniques described herein with respect to FIGS. 4, 5A-5B, and 6. In particular, the ultrasound image 700 may be generated using one or more sub-apertures and/or beam steering angles, as well as incoherent combination of the resulting subframes. To that end, the ultrasound image 700 may be produced by the signal pathway 600 of FIG. 6. As further shown, the ultrasound image 700 is shown with respect to an axial distance in centimeters (cm), which may represent a distance (e.g., a depth) from the transducer array, and a lateral distance, which may correspond to a position along the transducer array (e.g., a position of an acoustic element of the transducer array). The intensity of the ultrasound imaging data (e.g., the received echoes) is also shown in decibels (dB) according to the color-coded scale 702.

In comparison with the ultrasound image 300 of FIG. 3, the speckle present in the ultrasound image 700 is reduced. In particular, the region 710 (e.g., a near-field region) of the ultrasound image 700 is less distorted than the region 310 of the ultrasound image 300. This improvement in image quality may result from the incoherent combination of data corresponding to subframes of the ultrasound image 700. More specifically, because multiple subframes may include data associated with a particular location in an image field (e.g., as illustrated in FIGS. 5A-5B), the combination of the subframes may smooth (e.g., average) noise, such as speckle, out of the resulting, compounded image.

While the speckle is reduced in the near-field portions of the ultrasound image 700, as the depth of the ultrasound image 700 increases, the resolution decreases, as similarly described above with reference to FIG. 3. Accordingly, in some embodiments, additional or alternative techniques may be employed to improve the resolution of an ultrasound image. For instance, the resolution of an ultrasound image may depend in part on phase interferences between subframes compounded in the image. To that end, because incoherent combination is performed without phase information for the subframes, mechanisms of coherently combining data corresponding to subframes to generate a better resolved ultrasound image are described herein.

Figure 8:
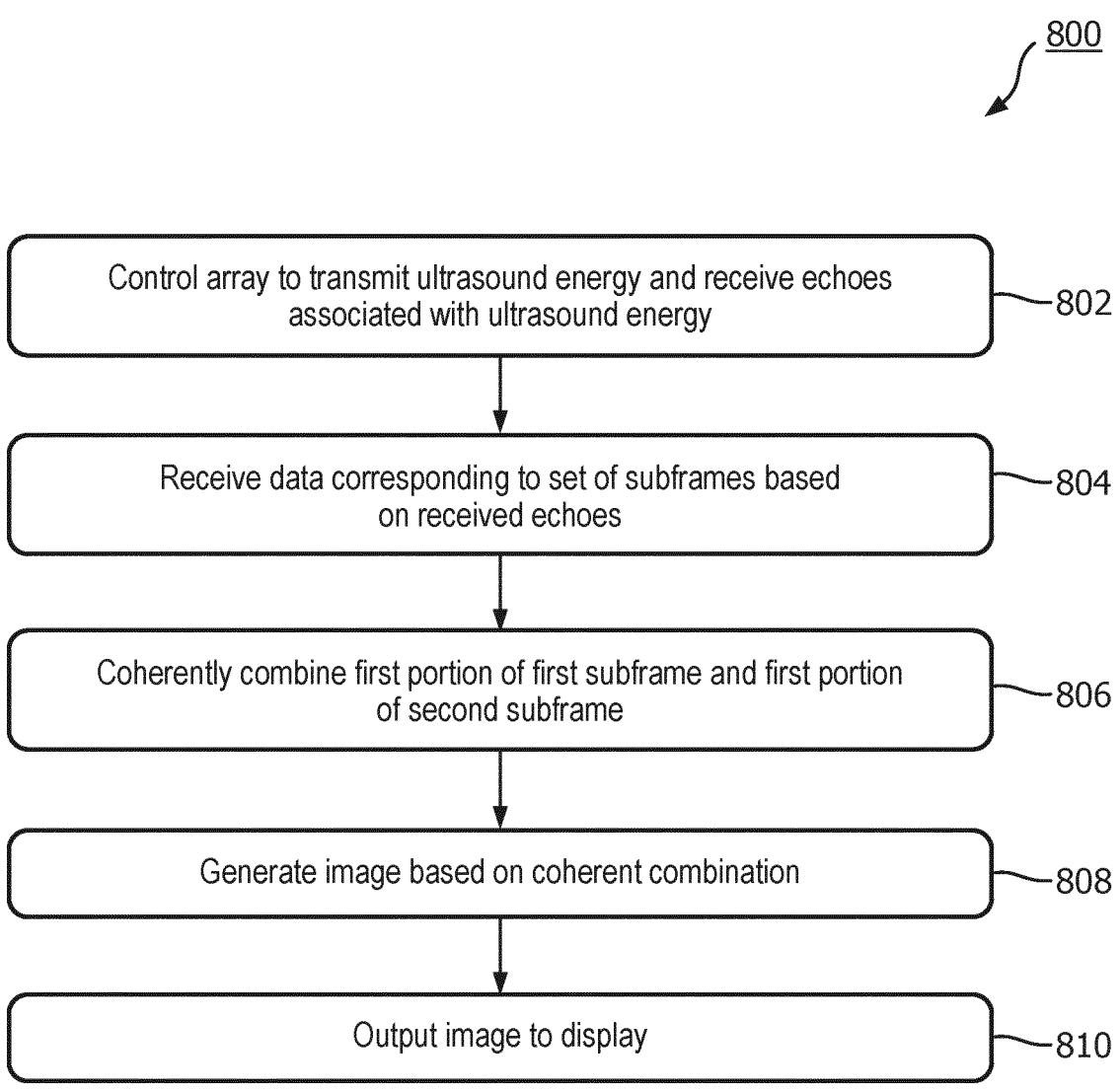
FIG. 8 is a flow diagram of a method for coherently combining data corresponding to a set of subframes to generate an ultrasound image, according to aspects of the present disclosure.

FIG. 8 is a flow diagram of a method 800 of coherently combining data corresponding to a set of subframes to generate an ultrasound image (e.g., a compounded ultrasound image), according to aspects of the present disclosure. As illustrated, the method 800 includes a number of enumerated steps, but embodiments of the method 800 may include additional steps before, after, or in between the enumerated steps. In some embodiments, one or more of the enumerated steps may be omitted, performed in a different order, or performed concurrently. The steps of the method 800 can be carried out by any suitable component within the ultrasound imaging system 100 and all steps need not be carried out by the same component. In some embodiments, one or more steps of the method 800 can be performed by, or at the direction of, a processor circuit of the ultrasound imaging system 100, including, e.g., the processor 260 (FIG. 2) or any other component.

At step 802, the method 800 includes controlling an array of acoustic elements to transmit ultrasound energy and receive echoes associated with ultrasound energy. In some embodiments, for example, the ultrasound imaging system 100 may control the transducer array 112 of the probe 110 to transmit first ultrasound energy using a first subset of the array of acoustic elements (e.g., a first sub-aperture) and to transmit second ultrasound energy using a second subset of the array of acoustic elements (e.g., a second sub-aperture). The first subset may be different from the second subset. In some cases, the first subset and the second subset may be entirely distinct (e.g., spaced from one another) or may overlap (e.g., share acoustic elements). Further, step 802 may involve receiving echoes associated with the first ultrasound energy and echoes associated with the second ultrasound energy, which may correspond to a first subframe and a second subframe, respectively. For instance, a first portion of the received echoes (e.g., the received echoes associated with the ultrasound energy) may correspond to the first ultrasound energy and a second portion of the received echoes may correspond to the second ultrasound energy. Moreover, in some embodiments, the array of acoustic elements may be controlled to receive the echoes associated with the first ultrasound energy using the first subset acoustic elements and to receive echoes associated with the second ultrasound energy using the second subset of acoustic elements.

At step 804, the method 800 may involve receiving data corresponding to set of subframes based on received echoes. The data corresponding to the set of subframes may include data corresponding to a first and a second subframe, which, as described above, may correspond to echoes associated with the first ultrasound energy and echoes associated with the second ultrasound energy, respectively. Moreover, the data corresponding to the first and second subframe may correspond to image data corresponding to the same object (e.g., an anatomical object) collected via respective sub-apertures and/or beam steering angles, as described above with reference to FIGS. 4 and 5A-5B. In some embodiments, the data corresponding to the set of subframes may be analog data, such as analog electrical signals from the array of acoustic elements. In some embodiments, the data corresponding to the set of subframes may be digital data. For instance, in such embodiments, the analog electrical signals from the array of acoustic elements may be sampled into a digital signal (e.g., digital data signal) by an ADC. Moreover, in some cases, the data corresponding to the set of subframes may be in the form of radio-frequency (RF) data. Further, the data corresponding to the set of subframes may include both phase and amplitude information.

At step 806, the method 800 may involve coherently combining a first portion of the first subframe and a first portion of the second subframe. More specifically, step 806 may involve coherently combining data corresponding to the first portion of the first subframe and data corresponding to the first portion of the second subframe. Both the data corresponding to the first portion of the first subframe and the data corresponding to the first portion of the second subframe may include phase information. That is, for example, to coherently combine the data corresponding to the first portion of the first subframe and the data corresponding to the first portion of the second subframe, the data corresponding to the first portion of the first subframe and the data corresponding to the first portion of the second subframe may be combined before envelope detection is performed on and/or phase information is removed from the data corresponding to the first portion of the first subframe and the data corresponding to the first portion of the second subframe. In some embodiments, the first portion of the first subframe and a first portion of the second subframe may be coherently combined by a GPU, which may be included in the host 130 and/or the probe 110, for example. Further, it may be appreciated that the first portion of the first subframe and the first portion of the second subframe may refer to the entire first and second subframe or a subset of pixels of the first and second subframe, respectively.

At step 808, the method 800 may involve generating an image (e.g., a compounded ultrasound image) based on the coherent combination of the first and second subframe. In some embodiments, the image may be generated based on beamforming, envelope detection, log compression, scan conversion, and/or the like of data corresponding to the first and second subframe. For instance, the image may be generated in accordance with a signal pathway within the ultrasound imaging system 100, as described with reference to FIG. 9.

Figure 9:
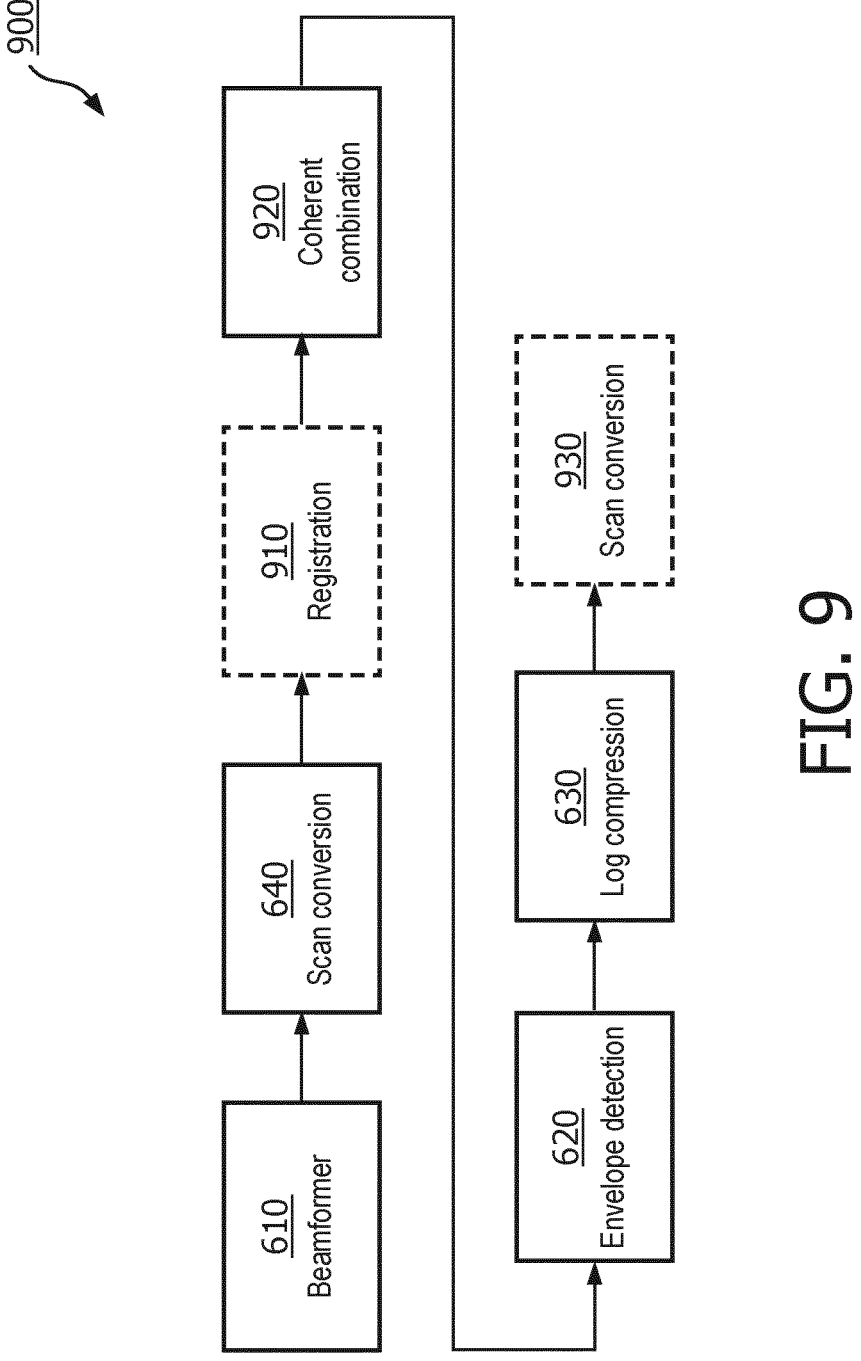
FIG. 9 is a block diagram of a signal pathway for generating an ultrasound image using coherent combination of a set of subframes, according to aspects of the present disclosure.

Turning now to FIG. 9, a signal pathway 900 that may be included in an ultrasound imaging system (e.g., ultrasound imaging system 100) and may be used to generate ultrasound image data and/or an ultrasound image is illustrated. In particular, the signal pathway 900 may be used to generate an ultrasound image based on the coherent combination of a set of subframes. The signal pathway 900 may be associated with a method, or process, for image generation. It will be understood that the elements of the signal pathway 900 may comprise computer program code or instructions executable by a processor circuit, such as the processor circuit 210 shown in FIG. 2. For example, in some embodiments, the elements of the signal pathway 900 comprise different processing (e.g., software) modules. In some embodiments, the elements of the signal pathway 900 comprise different hardware components.

In some embodiments, the components and/or operations of the signal pathway 900 are implemented by the probe 110 and/or the host 130 shown in FIG. 1. In particular, components of the signal pathway 900 may be implemented by the beamformer 114, the processor 116, the communication interface 118, the communication interface 136, and/or the processor 134. In some embodiments, for example, the components of the signal pathway 900 are distributed between the probe 110, and the host 130. Moreover, the components of the signal pathway 900 can be implemented via a combination of hardware and software components, and may be executed by the processor circuit 210 described above with respect to FIG. 2. For instance, in some embodiments, one or more components and/or operations of the signal pathway 900 can be executed by a GPU.

In some embodiments, ultrasound data may be received (e.g., input to) to the signal pathway 900. For instance, the signal pathway 900 may receive data corresponding to a set of subframes based on received echoes associated with ultrasound energy transmitted by an array of acoustic elements (e.g., transducer array 112). In particular, the data corresponding to the set of subframes may be associated with echoes associated with ultrasound energy transmitted by a set of sub-apertures and/or at a set of different angles, as described herein. The data corresponding to the set of subframes may include analog or digital data. For instance, in some cases, the signal pathway 900 may receive raw analog electrical signals from the array of acoustic elements. In such cases, one or more of the operations of the signal pathway 900 may be performed on the analog signals. Additionally or alternatively, the signal pathway 900 may include or be in communication with an analog-to-digital converter (ADC), which may sample the analog signals to provide digital subframe data.

As illustrated, the signal pathway 900 may include a beamformer 610. As described with reference to FIG. 6, the beamformer 610 may be substantially similar to the beamformer 114 of FIG. 1. To that end, the data corresponding to the set of subframes may be beamformed at the beamformer 610. For instance, the beamformer 610 may perform a coherent delay-and-sum operation on the data to provide beamformed signals.

After the data corresponding to the set of subframes is beamformed, the data corresponding to the set of subframes may be output to a scan conversion module 640. The scan conversion module 640 performs scan conversion on the image data (e.g., the data corresponding to the set of subframes) output by the beamformer 610 to a suitable format for coherent combination and/or registration. For instance, the scan conversion module 640 may convert the image data to a format that may be used by a processor circuit (e.g., processor circuit 210) to sum subframes and/or register subframes. Additionally or alternatively, the scan conversion module 640 may perform scan conversion on the image data to a suitable display format. For instance, the image data may be in a polar coordinate and the scan conversion module 640 may convert the image data into Cartesian coordinates for display. In some embodiments, a processor circuit, such as processor circuit 210 of FIG. 2, may implement the log compression module 630. In some embodiments, for example, a GPU may perform scan conversion on the data corresponding to a set of subframes.

Following scan conversion, the signal pathway 900 may include a registration module 910. As illustrated by the dashed border, the registration module 910 may optionally be included in the signal pathway 900. The registration module 910 may be implemented by a processor circuit (e.g., processor circuit 210), such as a GPU, to finely align subframes prior to summation (e.g., coherent combination). More specifically, the registration module 910 may spatially register the set of subframes with one another. This registration may involve identifying common and/or reference features across different subframes and associating the data points associated with these features with one another across the different subframes. In some embodiments, the registration may involve associating subframes obtained with the same sub-aperture and same beam steering angle with one another. Additionally or alternatively, the registration of subframes with one another may involve the use of data from another sensor or device, such as a position tracking system (e.g., an electromagnetic tracking system and/or an optical tracking system), that can identify the position of the ultrasound probe as each of the subframes are obtained. For instance, set of subframes may be associated with one another based on the determined position of the ultrasound probe.

In some embodiments, a mismatch may exist between subframes capturing the same feature. As an illustrative example, two subframes of the same object obtained using the same sub-aperture and same beam steering angle may vary from one another due to motion of a patient and/or the probe or another source of error (e.g., system and/or random error). Such mismatches may limit the effectiveness of coherent combination of subframes, as coherent combination may be sensitive to registration error. That is, for example, misalignment between subframes that are coherently combined may impact the interaction (e.g., interference) of phase information corresponding to the different subframes, which may result in the generation of a different ultrasound image than would otherwise be produced. In some embodiments, the misalignment may be reduced by calibrating the ultrasound imaging system 100. For instance, by imaging a point phantom, errors introduced by the probe 110 and/or the host 130 may be identified and calibration corrections may be applied for future imaging applications. To further correct the misalignment, after registering subframes with one another and/or with a location, the registration module 910 may adjust the data corresponding to the set of subframes to align the set of subframes with one another based on the registration. For instance, the registration module 910 may be configured to correct for misalignment resulting from motion in the set of subframes. In some embodiments, the registration module 910 may be configured to determine an adjustment (e.g., a correction factor) to correct for such misalignment based on consecutively obtained subframes that were collected using the same sub-aperture and beam steering angle. An example of motion detection and compensation (e.g., misalignment adjustments) is described in U.S. Pat. No. 9,345,455, filed Oct. 29, 2015, titled "Ultrasonic Synthetic Transmit Focusing with Motion Compensation," the entirety of which is hereby incorporated by reference.

The signal pathway 900 further includes a coherent combination module 920. The coherent combination module 920 may be configured to coherently combine (e.g., compound) the data corresponding to the set of subframes. For instance, the coherent combination module 920 may sum (e.g., average) data corresponding to a first subframe of the set of subframes and data corresponding to a second subframe of the set of subframes to coherently combine the data corresponding to the set of subframes. Moreover, coherent combination of image data may correspond to the summing (e.g., averaging) of data corresponding to the set of subframes that includes phase information. As such, the phase information from the first subframe may interact (e.g., interfere) with the phase information from the second subframe, when combined. Further, while the illustrated coherent combination module 920 is positioned at a particular point within the signal pathway 900, the coherent combination module 920 may additionally or alternatively be positioned in any portion of the signal pathway 900 where the data corresponding to the set of subframes includes phase information, such as any portion of the signal pathway 600 preceding envelope detection (e.g., at the envelope detection module 620).

In some embodiments, the coherent combination module 920 may be implemented as a summer, such as a digital or analog summer. Additionally or alternatively, a processor circuit, such as processor circuit 210 of FIG. 2, may implement the coherent combination module 920. In some embodiments, for example, a GPU may coherently combine data corresponding to a set of subframes.

Following coherent combination of the data corresponding to the set of subframes, envelope detection may be performed on the data corresponding to the set of subframes by the envelope detection module 620. As described above with reference to FIG. 6, the envelope detection module may be implemented as an envelope detector (e.g., a rectifier, a filter, and/or the like) that may output the envelope of the data corresponding to the set of subframes. Additionally or alternatively, the envelope detection may be performed by a beamformer (e.g., beamformer 114) and/or a processor circuit (e.g., processor circuit 210), such as a GPU.

The signal pathway 900 may further include a log compression module 630 configured to perform log compression on the data corresponding to the set of subframes. More specifically, the log compression module 630 may perform log compression on the data corresponding to the set of subframes after the envelope detection is performed (e.g., via the envelope detection module 620). In some embodiments, a processor circuit, such as processor circuit 210 of FIG. 2, may implement the log compression module 630. In some embodiments, for example, a GPU may perform log compression on the data corresponding to a set of subframes.

As further illustrated, the signal pathway 900 may optionally include an additional scan conversion module 930, which may be coupled to the log compression module 630. The scan conversion module 930 may be the same as or different from the scan conversion module 640. In some embodiments, the scan conversion module 930 may perform an additional scan conversion on the data corresponding to the set of subframes to optimize the format of the image data and/or complete the scan conversion of the image data. For instance, in some embodiments, the scan conversion module 640 may perform a partial scan conversion (e.g., a partial conversion, a conversion to an intermediate format, a conversion of a portion of the set of subframes) and the scan conversion module 930 may complete the scan conversion of the data corresponding to the set of subframes to a suitable format for display. In some embodiments, a processor circuit, such as processor circuit 210 of FIG. 2, may implement the scan conversion module 930. In some embodiments, for example, a GPU may perform scan conversion on the data corresponding to a set of subframes.

While the signal pathway 900 is illustrated and described herein as including a certain set of components and/or involving certain operations, embodiments are not limited thereto. To that end, additional components and/or operations may be included and/or components and/or operations may be omitted. For instance, the signal pathway 900 may additionally or alternatively include an ADC (e.g., involve analog-to-digital conversion), any suitable filter (e.g., a low pass filter, a high pass filter, a band pass filter, and/or the like), a buffer and/or memory device, which may temporarily store and/or duplicate data, and/or the like. In some embodiments, for example, image data may be buffered at a buffer until data corresponding to each of the set of subframes is received at the signal pathway 900 and/or received at a particular portion of the signal pathway 900. Moreover, while the signal pathway 900 is illustrated in a particular order, one or more of the components and/or operations may be performed in a different order or may be performed in parallel.

Figure 10:
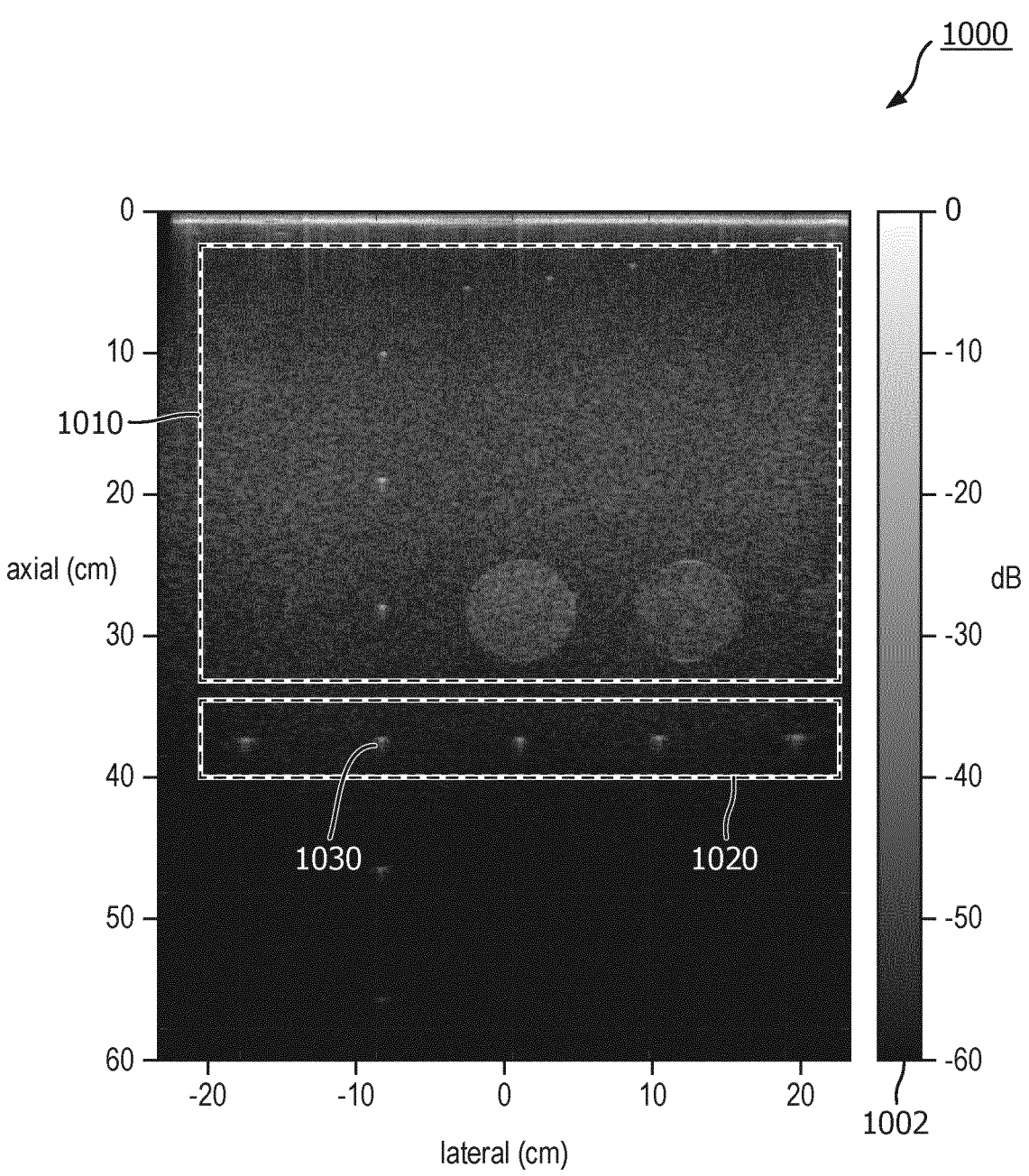
FIG. 10 is an ultrasound image, according to aspects of the present disclosure.

FIG. 10 illustrates an exemplary ultrasound image 1000 (e.g., a B-mode ultrasound image) generated based on coherent combination of data corresponding to a set of subframes, in accordance with the techniques described herein with respect to FIGS. 4, 5A-5B, 8, and 9. In particular, the ultrasound image 1000 may be generated using one or more sub-apertures and/or beam steering angles, as well as coherent combination of the resulting subframes. To that end, the ultrasound image 1000 may be produced by the signal pathway 900 of FIG. 9. As further shown, the ultrasound image 1000 is shown with respect to an axial distance in centimeters (cm), which may represent a distance (e.g., a depth) from the transducer array, and a lateral distance, which may correspond to a position along the transducer array (e.g., a position of an acoustic element of the transducer array). The intensity of the ultrasound imaging data (e.g., the received echoes) is also shown in decibels (dB) according to the color-coded scale 1002. In comparison with the ultrasound image 300 of FIG. 3, the resolution of the resolution of the ultrasound image 1000 is improved. In particular, the resolution within the region 1020 (e.g., a far-field region) of the ultrasound image 1000 is greater than the resolution within the corresponding region 320 and 720 of the ultrasound image 300 and the ultrasound image 700 (FIG. 7), respectively. For instance, the outline of the object 1030 is much sharper and more distinct than the outline of the object 330 and the object 730. In other words, the point spread of the object 1030 in the ultrasound image 1000 is minimized in comparison with the point spread of the object 330 and the object 730. More specifically, because multiple subframes may include data associated with a particular location in an image field (e.g., as illustrated in FIGS. 5A-5B), the coherent combination of the subframes may average point spread (e.g., resolution distortion), out of the resulting, compounded image.

While the resolution of the ultrasound image 1000 is visibly improved, especially in the far-field regions (e.g., region 1020), speckle remains present and apparent in the near-field portions (e.g., region 1010) of the ultrasound image 1000. That is, for example, the speckle (e.g., noise) within the region 1010 is greater than the speckle within the region 710 of the ultrasound image 700 and does not substantially vary from the speckle within the region 310 of the ultrasound image 300. Accordingly, in some embodiments, a combination of the techniques described herein may be employed to both improve the resolution and reduce the speckle present in an ultrasound image.

Returning now to FIG. 8, in some embodiments, generation of the image (e.g., at step 808) may be performed based on coherent combination of data corresponding to the subframes and the incoherent combination of data corresponding to the subframes. For instance, in some embodiments, a first image may be generated based on coherent combination of the data corresponding to the subframes, a second image may be generated based on incoherent combination of the data corresponding to the subframes, and the image (e.g., a third image) may be based on the combination of the first and second image, as described in greater detail below with reference to FIG. 11. The first and second image may be used to form the third image based on the application of pixel-level weights (e.g., masking) to the first and second image and the summation of the weighted images, for example. Additionally or alternatively, the image may be generated based on coherently summing a first portion of the data corresponding to the set of subframes, incoherently summing a second portion of the data corresponding to the set of subframes, and combining the first and second portions to form the image, as described in greater detail below with reference to FIG. 12. For instance, each of the portions may correspond to a respective subset of the set of subframes and/or a subset of the data corresponding to a particular subframe (e.g., data corresponding to a region or set of pixels within a subframe). As an illustrative example, out of ten subframes, five subframes may be summed coherently, the remaining five subframes may be summed incoherently, and the image may be formed based on the two summations. As an additional illustrative example, a top half of two subframes may be summed incoherently while a bottom half of the two subframes may be summed coherently, and an image may be formed from these two summations.

Figure 11:
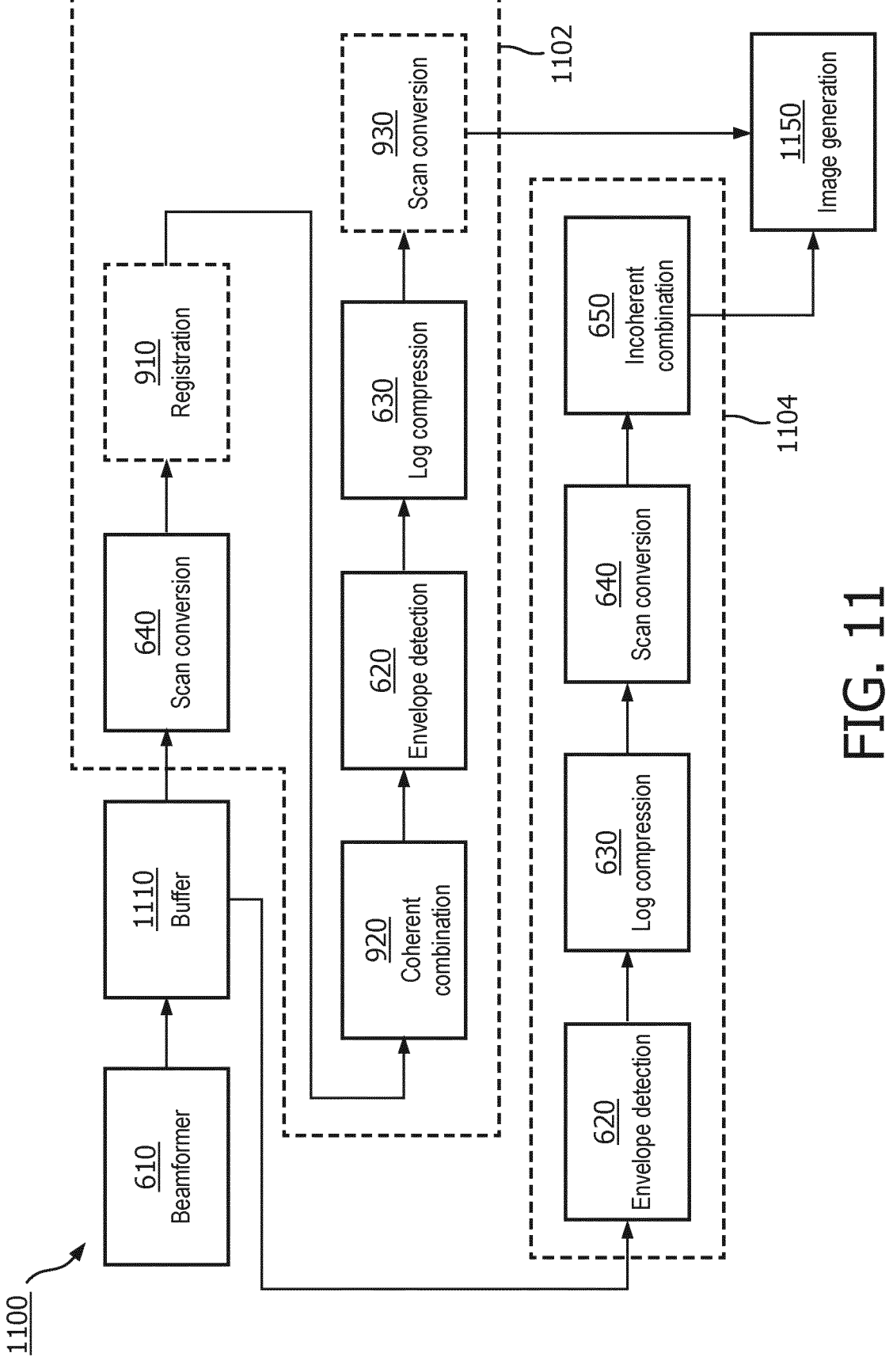
FIG. 11 is a block diagram of a signal pathway for generating an ultrasound image data based on coherent combination of a set of subframes and incoherent combination of the set of subframes, according to aspects of the present disclosure.

FIG. 11 is a block diagram of a signal pathway 1100 that may be included in an ultrasound imaging system (e.g., ultrasound imaging system 100) and may be used to generate ultrasound image data and/or an ultrasound image. In particular, the signal pathway 1100 may be used to generate an ultrasound image based on the coherent combination of a set of subframes and the incoherent combination of the set of subframes. The signal pathway 1100 may be associated with a method, or process, for image generation. It will be understood that the elements of the signal pathway 1100 may comprise computer program code or instructions executable by a processor circuit, such as the processor circuit 210 shown in FIG. 2. For example, in some embodiments, the elements of the signal pathway 1100 comprise different processing (e.g., software) modules. In some embodiments, the elements of the signal pathway 1100 comprise different hardware components.

In some embodiments, the components and/or operations of the signal pathway 1100 are implemented by the probe 110 and/or the host 130 shown in FIG. 1. In particular, components of the signal pathway 1100 may be implemented by the beamformer 114, the processor 116, the communication interface 118, the communication interface 136, and/or the processor 134. In some embodiments, for example, the components of the signal pathway 1100 are distributed between the probe 110, and the host 130. Moreover, the components of the signal pathway 1100 can be implemented via a combination of hardware and software components, and may be executed by the processor circuit 210 described above with respect to FIG. 2. For instance, in some embodiments, one or more components and/or operations of the signal pathway 1100 can be executed by a GPU.

In some embodiments, ultrasound data may be received (e.g., input to) to the signal pathway 1100. For instance, the signal pathway 1100 may receive data corresponding to a set of subframes based on received echoes associated with ultrasound energy transmitted by an array of acoustic elements (e.g., transducer array 112). In particular, the data corresponding to the set of subframes may be associated with echoes associated with ultrasound energy transmitted by a set of sub-apertures and/or at a set of different angles, as described herein. The data corresponding to the set of subframes may include analog or digital data. For instance, in some cases, the signal pathway 1100 may receive raw analog electrical signals from the array of acoustic elements. In such cases, one or more of the operations of the signal pathway 1100 may be performed on the analog signals. Additionally or alternatively, the signal pathway 1100 may include or be in communication with an analog-to-digital converter (ADC), which may sample the analog signals to provide digital subframe data.

Briefly, the signal pathway 1100 may include a first signal path 1102, which may be implemented to generate first image data based on coherent combination of the data corresponding to the set of subframes, and a second signal path 1104, which may be implemented to generate second image data based on the incoherent combination of the data corresponding to the set of subframes. The signal pathway 1100 may further be implemented to generate an ultrasound image based on the first and second image data (e.g., via an image generation module 1150). As illustrated, along with the beamformer 610, the first signal path 1102 may be substantially similar to the signal pathway 900 illustrated in FIG. 9, and the second signal path 1104 may be substantially similar to the signal pathway 600 illustrated in FIG. 6. Thus, for the sake of brevity, details of the components of the first signal path 1102 and the second signal path 1104 described above with reference to FIGS. 9 and 6, respectively, will not be repeated.

In some embodiments, the signal pathway 1100 may include a buffer 1110. The buffer 1110 may include a memory device configured to temporarily store the beamformed image data (e.g., received from the beamformer 610) for further processing. The buffer 1110 may comprise a volatile memory resource that is either accessible to a single processing unit (e.g., CPU core or FPGA) or a shared memory accessible to multiple processors (e.g., multiple cores, GPU, and/or multiple paths within an FPGA). In some embodiments, the buffer 1110 comprises a duplicator configured to duplicate the image data to be processed along different processing paths, such as the first signal path 1102 and the second signal path 1104.

After receiving respective image data from the buffer 1110, the first signal path 1102 may produce first image data based on coherent combination of the data corresponding to the set of subframes, and the second signal path 1104 may produce second image data based on incoherent combination of the data corresponding to the set of subframes. In this way, the first signal path 1102 may produce image data substantially similar to the ultrasound image 1000 of FIG. 10, and the second signal path may produce image data substantially similar to the ultrasound image 700 of FIG. 7. In some embodiments, the processing paths may be configured to perform operations on the respective image data simultaneously (e.g., in parallel) or at different times.

The first image data and the second image data may be received at the image generation module 1150, which may combine the first image data and the second image data to generate a compounded ultrasound image. In some embodiments, the image generation module 1150 may combine the first image data and the second image data by summing the data together to form the ultrasound image. In some embodiments, the image generation module 1150 may weight (e.g., mask) data in the first image data and/or the second image data and may perform a weighted summation of the datasets. As an illustrative example, pixel-level weighting, such as linear or non-linear weighting, may be applied to data corresponding to pixels within the first and/or second image data. In particular, the first image data and/or the second image data may be weighted based on a spatial frequency of pixels within the image data, a location (e.g., a depth) of the pixels within the data, and/or the like.

In the case of spatial frequency-based weighting, pixels associated with a relatively lower spatial frequency may be weighted such that the second image data (e.g., the incoherently summed imaged data) may have a greater contribution in the image than the first image data (e.g., the coherently summed image data), while pixels associated with a relatively higher spatial frequency may be weighted such that the first image data (e.g., the coherently summed image data) may have a greater contribution in the image than the second image data (e.g., the incoherently summed data). The pixels associated with the lower spatial frequency may correspond to the background of the ultrasound image, while the pixels associated with the higher spatial frequency may correspond to edges (e.g., borders) within the ultrasound image. In some embodiments, the spatial frequency of pixels may be determined based on filters (e.g., high and/or low pass filters) applied to the pixel data and/or other image processing techniques, such as a pixel level analysis to evaluate whether there is a change in the color of a pixel (e.g., correspond to an edge of an object). By weighting the first and second image data as described above, speckle may be smoothed out of the background of the image via incoherent combination of subframe data and the point spread at the borders of imaged objects may be minimized (e.g., the resolution of the imaged objects may be improved) via coherent combination of subframe data.

With respect to weighting based on location (e.g., axial depth), pixels at a relatively shallower depth (e.g., nearer-field) may be weighted such that the second image data (e.g., the incoherently summed imaged data) may have a greater contribution in the image than the first image data (e.g., the coherently summed image data), while pixels at a relatively greater depth (e.g., farther-field) may be weighted such that the first image data (e.g., the coherently summed image data) may have a greater contribution in the image than the second image data (e.g., the incoherently summed data). In some cases, speckle may be more apparent in the near-field (e.g., relatively shallower depth) of an ultrasound image and relatively less apparent in the far-field (e.g., relatively greater depth) of the image. For instance, ultrasound energy propagating through a medium (e.g., an anatomical object) may have a relatively high energy in a near-field region of the medium, and this energy may attenuate (e.g., decrease) as the ultrasound energy travels farther (e.g., through a far-field region of the medium). Because greater energy levels may result in resulting in greater random scattering, the near-field may include more speckle than the far-field. Moreover, the resolution of an ultrasound image may decrease as the depth of an image increases (e.g., as the distance from the aperture used to obtain the ultrasound image increases). Accordingly, resolution in the far-field of an image may be lower than resolution in the near-field of the image. Thus, by weighting the first and second image data as described above, speckle may be smoothed out of the near-field of the image via incoherent combination of subframe data and the resolution of the image objects may be improved in the far-field via coherent combination of subframe data.

In some embodiments, the image generation module 1150 may be implemented as a summer, such as a digital or analog summer. Additionally or alternatively, a processor circuit, such as processor circuit 210 of FIG. 2, may implement the image generation module 1150. In some embodiments, for example, a GPU may determine a weighting for the first and/or second image data and may then combine the weighted first and/or second image data to generate the image.

While the signal pathway 1100 is illustrated and described herein as including a certain set of components and/or involving certain operations, embodiments are not limited thereto. To that end, additional components and/or operations may be included and/or components and/or operations may be omitted. For instance, the signal pathway 1100 may additionally or alternatively include an ADC (e.g., involve analog-to-digital conversion), any suitable filter (e.g., a low pass filter, a high pass filter, a band pass filter, and/or the like), and/or the like. Further, while certain components and/or operations of the signal pathway 1100 are illustrated as duplicated across the first signal path 1102 and the second signal path 1104, it may be appreciated that the first signal path 1102 and the second signal path 1104 may share one or more components and/or operations in common. As an illustrative example, instead of including the scan conversion module 640 and/or scan conversion module 930 in the first path 1102 and a scan conversion module 640 in the second path 1104, a common scan conversion module may be used prior to the buffer 1110, on the output of the image generation module 1150, and/or the like. Moreover, while the signal pathway 1100 is illustrated in a particular order, one or more of the components and/or operations may be performed in a different order or may be performed in parallel. Additionally, the signal pathway 1100 may additionally or alternatively be employed to coherently sum a first portion of the along the first signal path 1102, incoherently sum a second portion of the data corresponding to the set of subframes along the second signal path 1104, and generate an image based on the first and second portion at the image generation module 1150.

Figure 12:
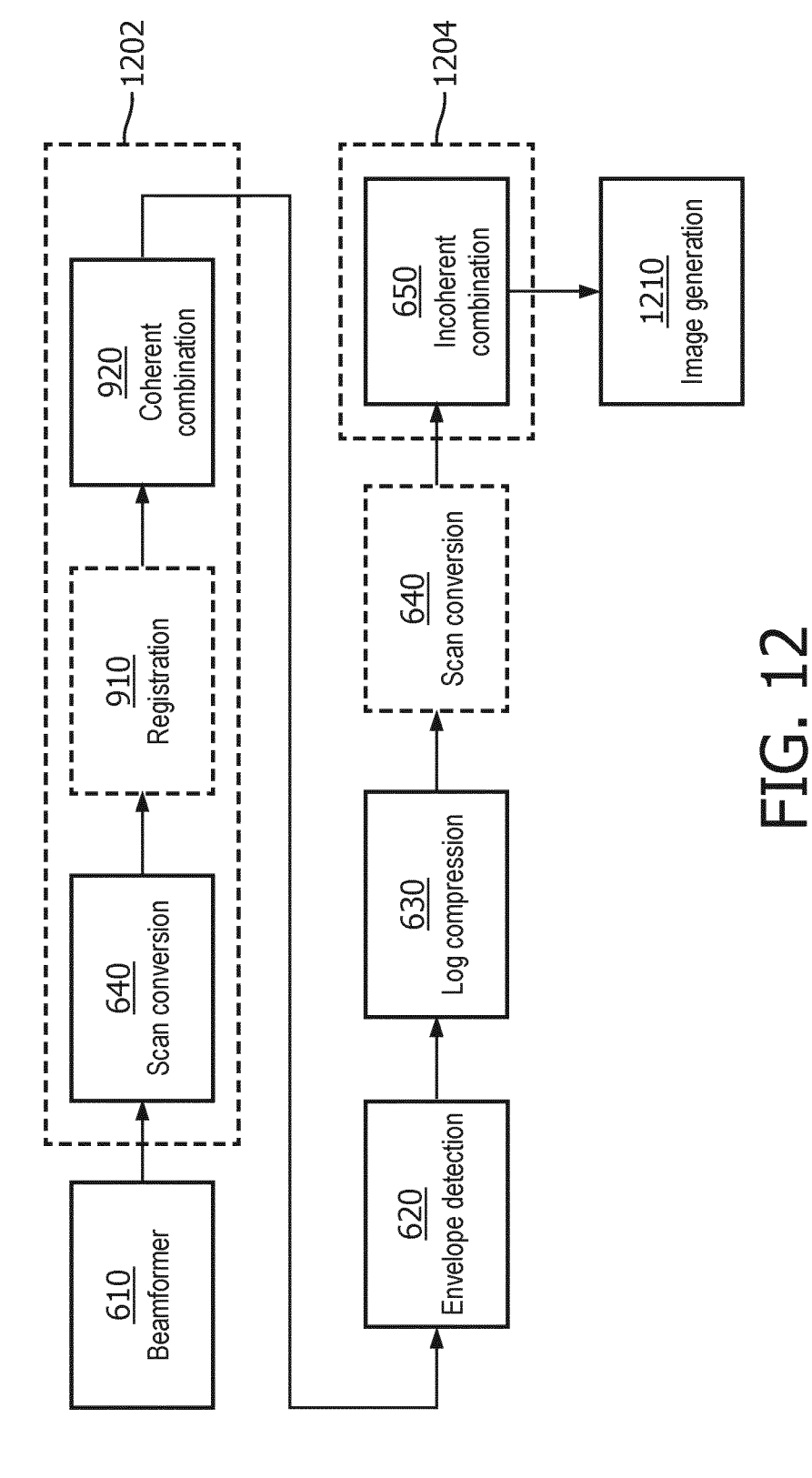
FIG. 12 is a block diagram of a signal pathway for generating an ultrasound image data based on coherent combination of a first portion of a set of subframes and incoherent combination of a second portion of the set of subframes, according to aspects of the present disclosure.

FIG. 12 is a block diagram of a signal pathway 1200 that may be included in an ultrasound imaging system (e.g., ultrasound imaging system 100) and may be used to generate ultrasound image data and/or an ultrasound image. In particular, the signal pathway 1200 may be used to generate an ultrasound image based on the coherent combination of a first portion of a set of subframes and the incoherent combination of a second portion of the set of subframes. The signal pathway 1200 may be associated with a method, or process, for image generation. It will be understood that the elements of the signal pathway 1200 may comprise computer program code or instructions executable by a processor circuit, such as the processor circuit 210 shown in FIG. 2. For example, in some embodiments, the elements of the signal pathway 1200 comprise different processing (e.g., software) modules. In some embodiments, the elements of the signal pathway 1200 comprise different hardware components.

In some embodiments, the components and/or operations of the signal pathway 1200 are implemented by the probe 110 and/or the host 130 shown in FIG. 1. In particular, components of the signal pathway 1200 may be implemented by the beamformer 114, the processor 116, the communication interface 118, the communication interface 136, and/or the processor 134. In some embodiments, for example, the components of the signal pathway 1200 are distributed between the probe 110, and the host 130. Moreover, the components of the signal pathway 1200 can be implemented via a combination of hardware and software components, and may be executed by the processor circuit 210 described above with respect to FIG. 2. For instance, in some embodiments, one or more components and/or operations of the signal pathway 1200 can be executed by a GPU.

In some embodiments, ultrasound data may be received (e.g., input to) to the signal pathway 1200. For instance, the signal pathway 1200 may receive data corresponding to a set of subframes based on received echoes associated with ultrasound energy transmitted by an array of acoustic elements (e.g., transducer array 112). In particular, the data corresponding to the set of subframes may be associated with echoes associated with ultrasound energy transmitted by a set of sub-apertures and/or at a set of different angles, as described herein. The data corresponding to the set of subframes may include analog or digital data. For instance, in some cases, the signal pathway 1200 may receive raw analog electrical signals from the array of acoustic elements. In such cases, one or more of the operations of the signal pathway 1200 may be performed on the analog signals. Additionally or alternatively, the signal pathway 1200 may include or be in communication with an analog-to-digital converter (ADC), which may sample the analog signals to provide digital subframe data.

As illustrated, the signal pathway 1200 includes a single processing path. In some embodiments, the signal pathway 1200 may be implemented to coherently sum a first portion of the data corresponding to the set of subframes and to incoherently sum a second portion of the data corresponding to the set of subframes. As described herein, the first portion of the data corresponding to the set of subframes and the second portion of the data corresponding to the set of subframes may correspond to a first subset of the set of subframes and a second subset of the set of subframes, respectively. Additionally or alternatively, the first portion of the data corresponding to the set of subframes and the second portion of the data corresponding to the set of subframes may correspond to a first region (e.g., pixel region) of the set of subframes and a second region of the set of subframes, respectively. For instance, the first and second region may correspond to a respective group of pixels, such as the pixels included in the top or bottom half of a subframe, pixels having a certain characteristic (e.g., location, spatial frequency, and/or the like).

One or more components and/or operations associated with the signal pathway 1200 may be applicable to the first portion of the data corresponding to the set of subframes, the second portion of the data corresponding to the set of subframes, or both. For instance, the signal pathway 1200 may include a coherent portion 1202 that, as illustrated, includes components and operations associated with the coherent combination of the first portion of the data corresponding to the set of subframes, as well as an incoherent portion 1204 that is associated with the incoherent combination of the second portion of the data corresponding to the set of subframes. The signal pathway 1200 also includes components and/or operations, such as the beamformer 610, envelope detection module 620, log compression module 630, and the scan conversion module 640, that may be associated with both the first and second portion of the data corresponding to the set of subframes. More specifically, components of the coherent portion 1202 may be configured to perform operations on the first portion of the data corresponding to the set of subframes and to refrain from performing operations on the second portion of the data corresponding to the set of subframes, components of the incoherent portion 1204 may be configured to perform operations on the second portion of the data corresponding to the set of subframes and to refrain from performing operations on the first portion of the data corresponding to the set of subframes, and the remaining components of the signal pathway 1200 may be configured to perform operations on both the first and second portions of the data corresponding to the set of subframes As illustrated, after the data corresponding to the set of subframes (e.g., both the first and second portion of the data) is beamformed at the beamformer 610, as described above with reference to FIGS. 6 and 9, the first portion of the data corresponding to the set of subframes may be coherently combined via the coherent portion 1202 of the signal pathway 1200. In particular, the first portion of the data corresponding to the set of subframes may be coherently combined via the coherent combination module 920, and in preparation for the coherent combination, the first portion of the data corresponding to the set of subframes may be scan converted and/or corrected for registration errors (e.g., motion) via the scan conversion module 640 and/or the registration module 910, respectively, as described with reference to FIG. 9.

In some embodiments, envelope detection may be performed on the second portion of the data corresponding to the set of subframes, as well as the coherently combined first portion of the data corresponding to the set of subframes at the envelope detection module 620. Similarly, log compression may be performed on each of these datasets at the log compression module 630. Subsequently, scan conversion may be performed on the second portion of the data corresponding to the set of subframes at the scan conversion module 640 and may optionally be performed on the coherently combined first portion of the data corresponding to the set of subframes.

At the incoherent portion 1204 of the signal pathway 1200, the second portion of the data corresponding to the set of subframes may be incoherently combined via the incoherent combination module 650. The incoherently combined second portion of the data corresponding to the set of subframes and the coherently combined first portion of the data corresponding to the set of subframes may be used to generate a compounded ultrasound image at image generation module 1210. In some embodiments, for example, the image generation module 1210 may sum and/or combine the incoherently combined second portion of the data corresponding to the set of subframes and the coherently combined first portion of the data corresponding to the set of subframes into a single dataset to generate the image.

Figure 13:
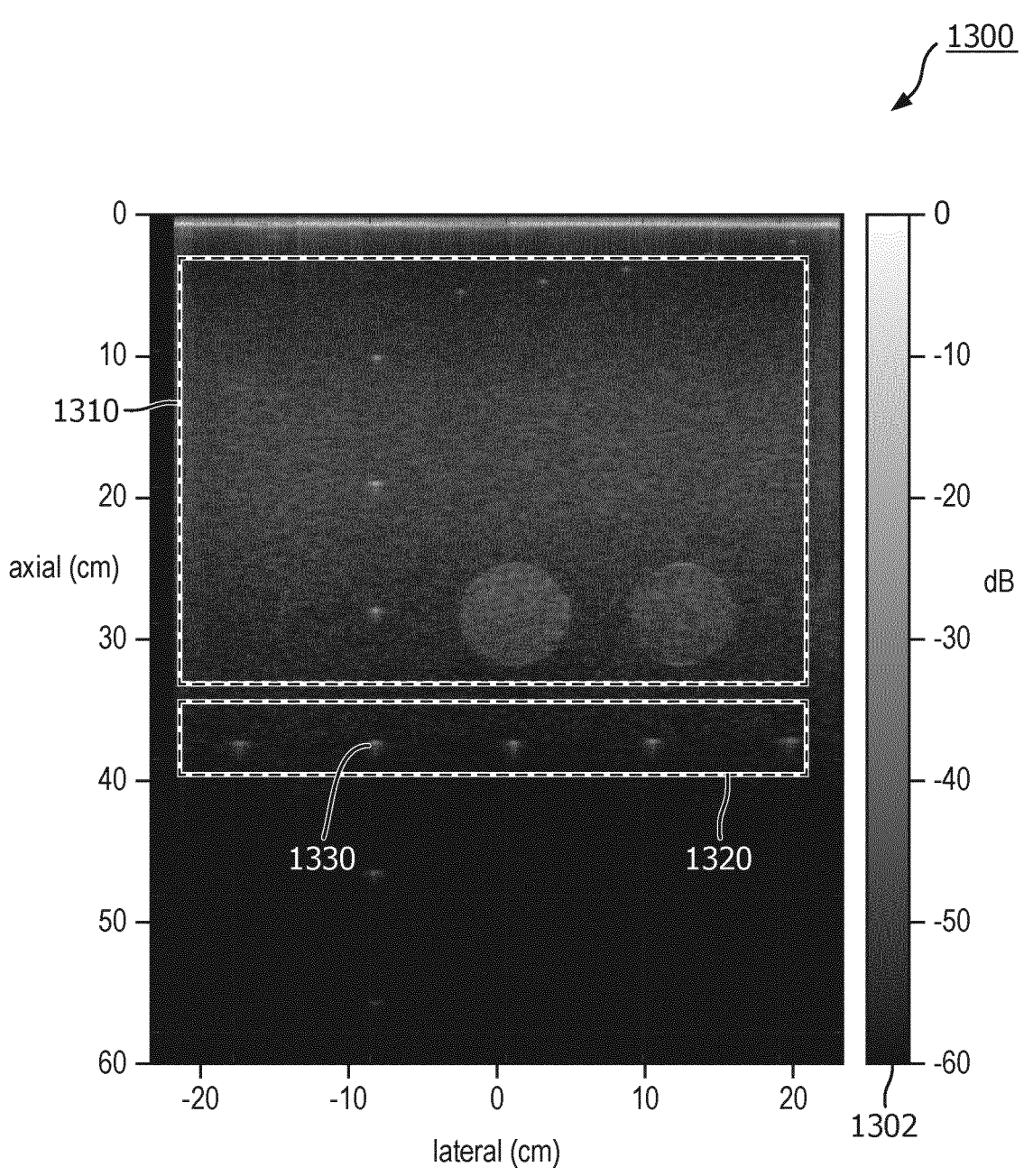
FIG. 13 is an ultrasound image, according to aspects of the present disclosure.

FIG. 13 illustrates an exemplary ultrasound image 1300 (e.g., a B-mode ultrasound image) generated based on both coherent and incoherent combination of data corresponding to a set of subframes, in accordance with the techniques described herein with respect to FIGS. 4, 5A-5B, 6, 8, 9, 11, and 12. In particular, the ultrasound image 1300 may be generated by blending (e.g., combining) coherently combined and incoherently combined image data (e.g., subframes) obtained using one or more sub-apertures and/or beam steering angles. To that end, the ultrasound image 1300 may be produced by the signal pathway 1100 of FIG. 11 and/or the signal pathway 1200 of FIG. 12. As further shown, the ultrasound image 1300 is shown with respect to an axial distance in centimeters (cm), which may represent a distance (e.g., a depth) from the transducer array, and a lateral distance, which may correspond to a position along the transducer array (e.g., a position of an acoustic element of the transducer array). The intensity of the ultrasound imaging data (e.g., the received echoes) is also shown in decibels (dB) according to the color-coded scale 1302.

In comparison with the ultrasound image 300 of FIG. 3, both the speckle present in the ultrasound image 1300 is reduced and the resolution of the ultrasound image 1300 is improved. In particular, the region 1310 (e.g., a near-field region) of the ultrasound image 1300 is less distorted than the region 310 of the ultrasound image 300, and the region 1320 (e.g., a far-field region) of the ultrasound image 1300 is more resolved. These improvements in image quality may result from the incoherent combination of data corresponding to the region 1310 and coherent combination of data corresponding to the region 1320, for example. Additionally or alternatively, the improvements may result from a greater weighting of incoherent combination of data in association with the region 1310 and/or the background of the image 1300 and greater weighting of coherent combination of data in association with the region 1320 and/or the edges included in the image 1300, for example As an illustrative example, the ultrasound image 700 of FIG. 7 and the ultrasound image 1000 of FIG. 10 may be combined to generate the ultrasound image 1300. That is, for example, the speckle reduction (e.g., via incoherent combination) produced by the generation of the ultrasound image 700 may be combined with the resolution improvement affected by the generation of the ultrasound image 1000 (e.g., via coherent combination) to generate the ultrasound image 1300.

Returning to FIG. 8, at step 810, the method 800 may involve outputting the image generated at step 808 to display. For instance, the image may be output to a display in communication with the host 130, such as display 132. Because, at step 808, the image may be generated based on coherent combination or a weighting between coherent and incoherent combination, outputting the image may involve outputting an image having features described above with reference to FIGS. 7, 10, and/or 13. That is, for example, step 810 may involve outputting an ultrasound image compounded based on coherent combination, incoherent combination, or both.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

The invention claimed is:

1. An ultrasound imaging system, comprising:
an array of acoustic elements configured to transmit ultrasound energy and receive echoes associated with the ultrasound energy; and
a processor circuit in communication with the array of acoustic elements and configured to:
receive data corresponding to a set of subframes based on the received echoes, wherein the set of subframes comprises a first subframe and a second subframe;
register a first portion of the first subframe with a first portion of the second subframe;
determine a correction for misalignment resulting from motion in the subframes before coherently combining data corresponding to the first portion of the first subframe and the data corresponding to the first portion of the second subframe;
coherently combine the data corresponding to the first portion of the first subframe and the data corresponding to the first portion of the second subframe, wherein the data corresponding to the first portion of the first subframe and the data corresponding to the first portion of the second subframe comprise phase information;
generate a first image based on the coherent combination of the first portion of the first subframe and the first portion of the second subframe;

generate a second image based on an incoherent combination of the first portion of the first subframe and the first portion of the second subframe;
combine the first image and the second image; and
output the combined image to a display in communication with the processor circuit.

2. The ultrasound imaging system of claim 1, wherein the ultrasound energy comprises first ultrasound energy and second ultrasound energy, and
wherein, to transmit the ultrasound energy, the array of acoustic elements is configured to:
transmit the first ultrasound energy using a first subset of the array of acoustic elements; and
transmit the second ultrasound energy using a second subset of the array of acoustic elements.

3. The ultrasound imaging system of claim 2, wherein the first subframe corresponds to the received echoes associated with the first ultrasound energy and the second subframe corresponds to the received echoes associated with the second ultrasound energy.

4. The ultrasound imaging system of claim 2, wherein, to receive the echoes associated with the ultrasound energy, the array of acoustic elements is configured to:
receive echoes associated with the first ultrasound energy using the first subset of the array of acoustic elements; and
receive echoes associated with the second ultrasound energy using the second subset of the array of acoustic elements.

5. The ultrasound imaging system of claim 1, wherein the processor circuit is configured to generate the combined image further based on an envelope detection of the coherent combination.

6. The ultrasound imaging system of claim 1, wherein the processor circuit is configured to generate the combined image further based on a log compression of the coherent combination.

7. The ultrasound imaging system of claim 1, wherein the processor circuit is configured to:
perform a scan conversion on the data corresponding to the set of subframes,
wherein the processor circuit is configured to coherently combine the data corresponding to the first portion of the first subframe and the data corresponding to the first portion of the second subframe further based on the scan conversion.

8. The ultrasound imaging system of claim 1, wherein the processor circuit is configured to:
incoherently combine data corresponding to a second portion of the first subframe and data corresponding to a second portion of the second subframe; and
generate the combined image further based on the incoherently combined data corresponding to the second portion of the first subframe and the second portion of the second subframe.

9. The ultrasound imaging system of claim 1, wherein the processor circuit is configured to combine the first image and the second image by a weighted summation, wherein weightings are determined based on a spatial frequency of pixels of the first portion of the first subframe.

10. The ultrasound imaging system of claim 1, wherein the processor circuit is configured to combine the first image and the second image by a weighted summation, wherein weightings are determined based on a location of the first portion of the first subframe within the first subframe.

11. The ultrasound imaging system of claim 1, wherein the processor circuit is configured to register the first portion of the first subframe with the first portion of the second subframe based on:

identifying a difference between the data corresponding to the first portion of the first subframe and data corresponding to a first portion of a third subframe of the set of subframes; and adjusting the data corresponding to the first portion of the first subframe based on the identified difference.

12. The ultrasound imaging system of claim 1, wherein the processor circuit comprises a graphics processing unit (GPU).

13. A method, comprising:

controlling, by a processor circuit, an array of acoustic elements in communication with the processor circuit to transmit ultrasound energy and receive echoes associated with the ultrasound energy;

receiving, by the processor circuit, data corresponding to a set of subframes based on the received echoes, wherein the set of subframes comprises a first subframe and a second subframe;

registering a first portion of the first subframe with a first portion of the second subframe;

determining a correction for misalignment resulting from motion in the subframes before coherently combining data corresponding to the first portion of the first subframe and the data corresponding to the first portion of the second subframe;

coherently combining, by the processor circuit, the data corresponding to the first portion of the first subframe and the data corresponding to the first portion of the second subframe, wherein the data corresponding to the first portion of the first subframe and the data corresponding to the first portion of the second subframe comprise phase information;

generating, by the processor circuit, a first image based on the coherent combination of the first portion of the first subframe and the first portion of the second subframe generating a second image based on an incoherent combination of the first portion of the first subframe and the first portion of the second subframe;

combining the first image and the second image; and outputting, by the processor circuit, the combined image to a display in communication with the processor circuit.

\*　\*　\*　\*　\*